(12) United States Patent
Yoshioka

(10) Patent No.: US 10,107,777 B2
(45) Date of Patent: *Oct. 23, 2018

(54) BIOLOGICAL INFORMATION MEASUREMENT DEVICE AND BIOLOGICAL INFORMATION MEASUREMENT METHOD USING SAME

(71) Applicant: Panasonic Healthcare Holdings Co., Ltd., Tokyo (JP)

(72) Inventor: Eriko Yoshioka, Ehime (JP)

(73) Assignee: PHC Holdings Corporation, Tokyo (JP)

( * ) Notice: Subject to any disclaimer, the term of this patent is extended or adjusted under 35 U.S.C. 154(b) by 103 days.

This patent is subject to a terminal disclaimer.

(21) Appl. No.: 15/197,019

(22) Filed: Jun. 29, 2016

(65) Prior Publication Data

US 2017/0023517 A1 Jan. 26, 2017

Related U.S. Application Data

(63) Continuation of application No. 14/406,039, filed as application No. PCT/JP2013/002743 on Apr. 23, 2013, now Pat. No. 9,410,916.

(30) Foreign Application Priority Data

Jun. 6, 2012 (JP) ................................ 2012-128576

(51) Int. Cl.
*G01N 27/327* (2006.01)

(52) U.S. Cl.
CPC ....... *G01N 27/3274* (2013.01); *G01N 27/327* (2013.01)

(58) Field of Classification Search
CPC ... C12Q 1/00; C12Q 1/02; C12Q 1/34; G01N 27/327–27/3274
See application file for complete search history.

(56) References Cited

U.S. PATENT DOCUMENTS

2004/0157337 A1 8/2004 Burke et al.
2004/0259264 A1 12/2004 Morita et al.
(Continued)

FOREIGN PATENT DOCUMENTS

CN   1575415    2/2005
CN   101393200  3/2009
(Continued)

OTHER PUBLICATIONS

Office Action issued in corresponding European Patent Application No. 13 801 340.4-1020, dated Feb. 22, 2018, 4 pages.

*Primary Examiner* — Maris R Kessel
(74) *Attorney, Agent, or Firm* — Hamre, Schumann, Mueller & Larson, P.C.

(57) ABSTRACT

In a biological information measurement device for measuring, for example, a blood glucose level, it is intended to improve measurement accuracy. In a voltage sweep mode A (a biological information characteristic detection mode), different voltage values are applied between a first input terminal and a second input terminal from a voltage applying unit 15 in a first period and a second period, a plurality of various factors that affect variation in the measurement of biological information are considered as changes in the current value in the voltage sweep mode A (the biological information characteristic detection mode), thereby a biological information correction value is calculated from the changes in the current value, and the biological information measurement value measured during the biological information measurement mode C is corrected by the biological information correction value. Thus, the measurement accuracy can be improved.

1 Claim, 20 Drawing Sheets

(56) References Cited

U.S. PATENT DOCUMENTS

| | | | |
|---|---|---|---|
| 2007/0131565 | A1 | 6/2007 | Fujiwara et al. |
| 2009/0184004 | A1 | 7/2009 | Chatelier et al. |
| 2010/0283488 | A1 | 11/2010 | Nakamura et al. |
| 2010/0327886 | A1 | 12/2010 | Nakamura et al. |

FOREIGN PATENT DOCUMENTS

| | | |
|---|---|---|
| JP | 2005-017183 | 1/2005 |
| JP | 2005-147990 | 6/2005 |
| JP | 2011-164116 | 8/2011 |
| WO | 03/060154 | 7/2003 |
| WO | 2005/054840 | 6/2005 |
| WO | 2009/119117 | 10/2009 |
| WO | 2009/119118 | 10/2009 |
| WO | 2012/017198 | 2/2012 |

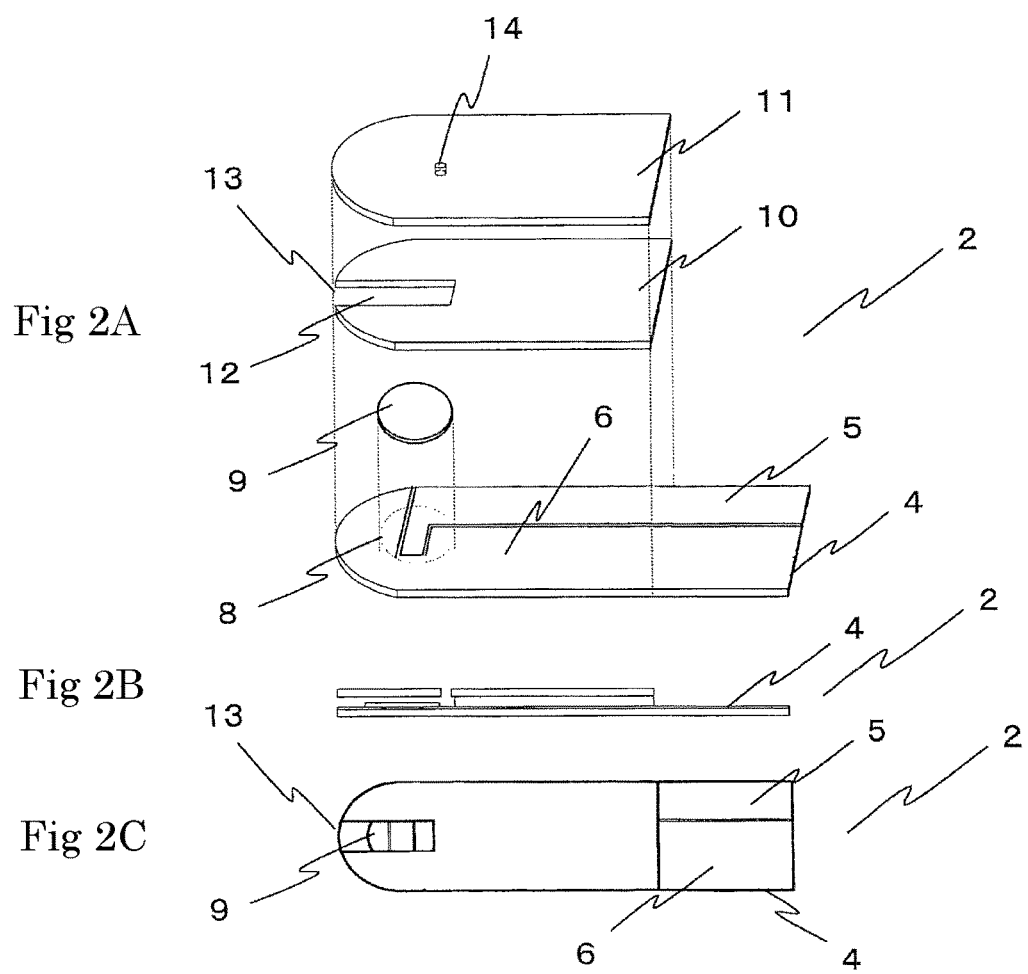

BIOLOGICAL INFORMATION MEASUREMENT DEVICE AND BIOLOGICAL INFORMATION MEASUREMENT METHOD USING SAME

TECHNICAL FIELD

The present invention relates to a biological information measurement device for measuring, for example, a blood glucose level, and a biological information measurement method using the same.

BACKGROUND ART

A conventional biosensor for measuring, for example, a blood glucose level is configured to have a first electrode, a second electrode, and a reagent portion provided between the first electrode and the second electrode.

A biological information measurement device, to which the biosensor is attached, has been configured as follows.

That is, it has been configured to be provided with a first input terminal, to which the first electrode of the biosensor is connected, a second input terminal, to which the second electrode is connected, a voltage applying unit that applies a voltage to the first input terminal and the second input terminal, and a control unit that is connected to the voltage applying unit, the first input terminal, and the second input terminal (for example, Patent Document 1 mentioned below).

PRIOR ART DOCUMENTS

Patent Documents

[Patent Document 1] JP 2005-017183 A

DISCLOSURE OF INVENTION

Problem to be Solved by the Invention

In the aforementioned conventional example, the biosensor is attached to the biological information measurement device, then a drop of blood is applied to the biosensor as a biological sample, and thereafter, the blood glucose level is measured as biological information. However, depending on the individual differences, storage conditions of the biosensor, variation in the temperature of the biosensor reaction part, technique of applying a drop of blood, etc., variation in the blood glucose level measured may occur, resulting in a low measurement accuracy.

Therefore, it is an object of the present invention to improve the accuracy in measuring biological information.

Means for Solving Problem

In order to attain this object, the present invention provides a biological information measurement device, to which a biosensor is attached, the biosensor having a first electrode, a second electrode, and a reagent portion provided between the first electrode and the second electrode, wherein the biological information measurement device includes: a first input terminal, to which the first electrode is connected; a second input terminal, to which the second electrode is connected; a voltage applying unit for applying a voltage to the first input terminal and the second input terminal; and a control unit connected to the voltage applying unit, the first input terminal, and the second input terminal, the control unit is configured to execute a biological information characteristic detection mode and a biological information measurement mode following the biological information characteristic detection mode, and during the biological information characteristic detection mode, with respect to the voltage applying unit, the control unit applies different voltage values between the first input terminal and the second input terminal from the voltage applying unit in a first period and a second period of the biological information characteristic detection mode and detects currents flowing between the first input terminal and the second input terminal in the first period and the second period, calculates a biological information correction value from the currents flowing between the first input terminal and the second input terminal in the first period and the second period, and corrects a biological information measurement value measured by the biological information correction value during the biological information measurement mode.

Thus, the desired object, i.e., the improvement in the accuracy in measuring biological information, is attained.

Effects of the Invention

As described above, the present invention provides a biological information measurement device, to which a biosensor is attached, the biosensor having a first electrode, a second electrode, and a reagent portion provided between the first electrode and the second electrode, wherein the biological information measurement device includes: a first input terminal, to which the first electrode is connected; a second input terminal, to which the second electrode is connected; a voltage applying unit for applying a voltage to the first input terminal and the second input terminal; and a control unit connected to the voltage applying unit, the first input terminal, and the second input terminal, the control unit is configured to execute a biological information characteristic detection mode and a biological information measurement mode following the biological information characteristic detection mode, and during the biological information characteristic detection mode, with respect to the voltage applying unit, the control unit applies different voltage values between the first input terminal and the second input terminal from the voltage applying unit in a first period and a second period of the biological information characteristic detection mode and detects currents flowing between the first input terminal and the second input terminal in the first period and the second period, calculates a biological information correction value from the currents flowing between the first input terminal and the second input terminal in the first period and the second period, and corrects a biological information measurement value measured by the biological information correction value during the biological information measurement mode, thus improving the measurement accuracy.

That is, the present invention is configured so that in the biological information characteristic detection mode, different voltage values are applied between the first input terminal and the second input terminal from the voltage applying unit in the first period and the second period and thereby a plurality of various factors that affect variation in the measurement of biological information are considered as changes in the current value in the biological information characteristic detection mode, the biological information correction value is calculated from the changes in the current value, and the biological information measurement value measured during the biological information measurement mode is corrected by the biological information correction value. Thus, the measurement accuracy can be improved.

In this regard, to describe further, the substances that are affected by the individual differences, storage conditions of the biosensor, variation in the temperature of the biosensor reaction part, technique of applying a drop of blood, etc, each react differently to different voltages. Therefore, as in the present invention, when different voltage values are applied between the first input terminal and the second input terminal from the voltage applying unit, the effects on the respective substances are detected beforehand and using the results thereof, the biological information measurement value measured during the biological information measurement mode is corrected.

BRIEF DESCRIPTION OF DRAWINGS

FIG. 2A is an exploded perspective view of a biosensor that is used for the biological information measurement device according to First Embodiment of the present invention. FIG. 2B is a side view of the biosensor that is used for the biological information measurement device according to First Embodiment of the present invention. FIG. 2C is a plan view of the biosensor that is used for the biological information measurement device according to First Embodiment of the present invention.

DESCRIPTION OF THE INVENTION

Hereinafter, embodiments of the present invention, each of which is adapted to a biological information measurement device for measuring the blood glucose level, are described using accompanying drawings.

<Embodiment 1>

Figure 1:
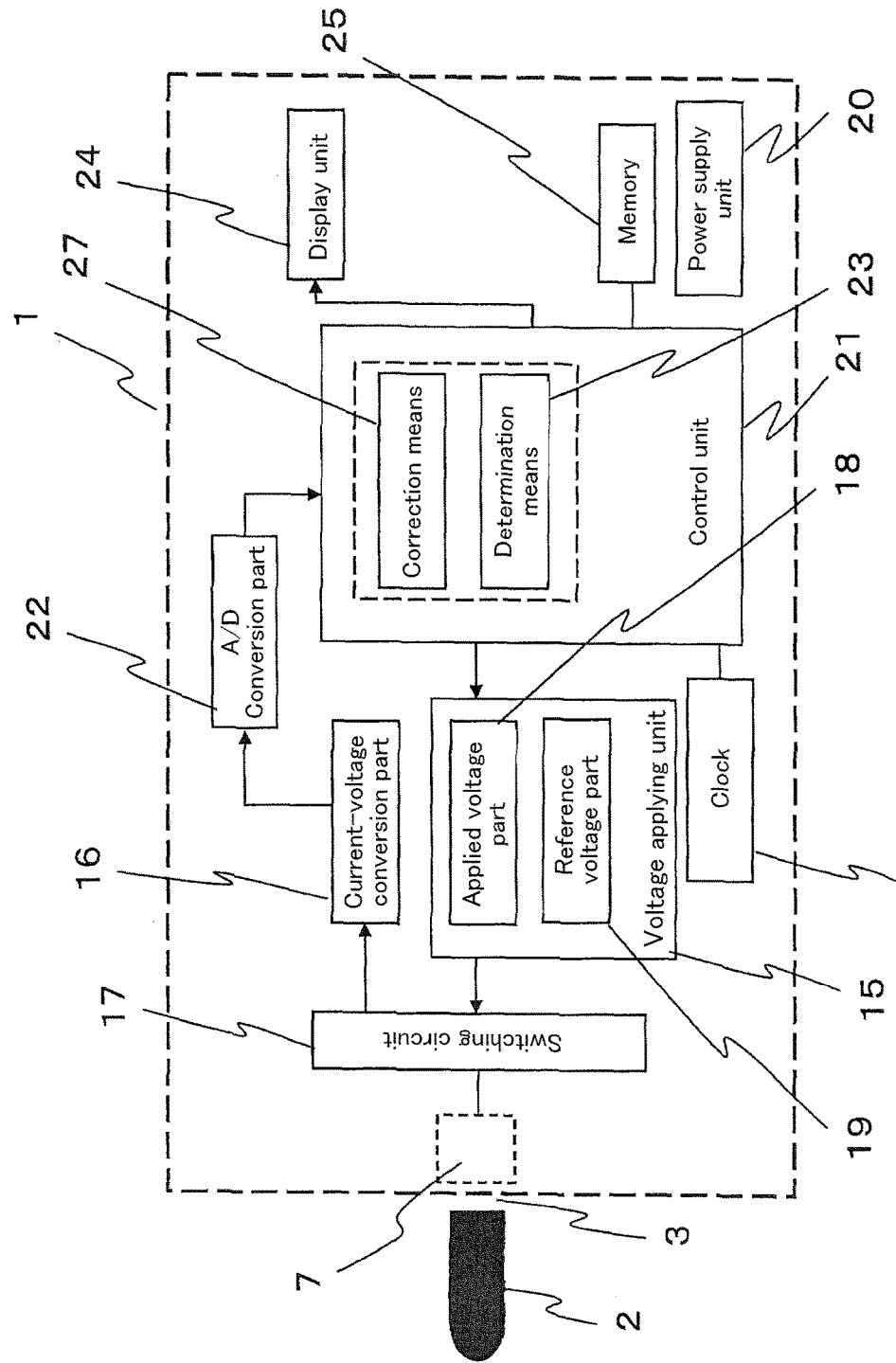
FIG. 1 is an electrical block diagram of a biological information measurement device according to First Embodiment of the present invention.

FIG. 1 is an electrical block diagram of a biological information measurement device according to First Embodiment of the present invention. FIG. 2A is an exploded perspective view of a biosensor that is used for the biological information measurement device according to First Embodiment of the present invention. FIG. 2B is a side view of the biosensor that is used for the biological information measurement device according to First Embodiment of the present invention. FIG. 2C is a plan view of the biosensor that is used for the biological information measurement device according to First Embodiment of the present invention. As shown in FIG. 1, in this biological information measurement device, a body case 1 is provided with an insertion opening 3 for a biosensor 2 on one end thereof.

As shown in FIG. 2A, the biosensor 2 is formed, with two electrodes, i.e., a blood component measurement working electrode (an example of the first electrode) 5 and a blood component measurement counter electrode (an example of the second electrode) 6, being arranged, on a rectangular-shaped insulating substrate 4, opposed to each other at a predetermined interval. Examples of the biological information to be measured by the biological information measurement device of the present invention include a glucose value, a lactic acid value, a uric acid level, a bilirubin level, and a cholesterol level. Furthermore, examples of the biological sample that is used for obtaining such biological information include blood, urine, and sweat. This biosensor 2 is an example in the case of using blood as the biological sample.

Parts of the blood component measurement working electrode 5 and the blood component measurement counter electrode 6 that are located on one end side (the right end side in FIG. 2) of the insulating substrate 4 are inserted into the body case 1 through the insertion opening 3 shown in FIG. 1 to come into contact with an input terminal portion 7 and thereby they are electrically connected to the biological information measurement device.

Furthermore, as shown in FIG. 2A, in this biosensor 2, a reagent portion 8 is disposed between the blood component measurement working electrode 5 and the blood component measurement counter electrode 6 on the other side of the biosensor 2 (on the opposite side to the portion to be inserted into the insertion opening 3).

In this biosensor 2, a reagent 9 is placed on the reagent portion 8. With this state, the blood component measurement working electrode 5 and the blood component measurement counter electrode 6 are connected to each other through the reagent 9 placed on the reagent portion 8. The reagent 9 contains oxidoreductase, such as glucose dehydrogenase, and a mediator (an electron carrier) and selectively contains, as optional components, a polymeric material, an enzyme stabilizer, a crystal homogenizer, etc.

Furthermore, a cover 11 is placed above the insulating substrate 4 and the reagent 9, with a spacer 10 being interposed therebetween. On one end side (on the right end side in FIG. 2) of the insulating substrate 4, parts of the blood component measurement working electrode 5 and the blood component measurement counter electrode 6 are exposed without being covered by the spacer 10 and the cover 11.

The exposed parts of the blood component measurement working electrode 5 and the blood component measurement counter electrode 6 are electrically connected to the input terminal portion 7 as described above.

In the spacer 10 of the biosensor 2, a blood supply path 12 for introducing blood is formed. This blood supply path 12 extends from the other end side (the left end side in FIG. 2) of the biosensor 2 to above the reagent 9, and the other end side that is open to the outside forms a blood supply port 13.

As described above, the blood component measurement working electrode 5 and the blood component measurement counter electrode 6 are electrically connected to the input terminal portion 7. Specifically, the blood component measurement working electrode 5 is connected to a first input terminal (not shown in the drawings) of the input terminal portion 7, and the blood component measurement counter electrode 6 is connected to a second input terminal (not shown in the drawings) of the input terminal portion 7.

Furthermore, as is understood also from FIG. 2, in this biosensor 2, the blood component measurement counter electrode 6 is arranged closest to the blood supply port 13, followed by the blood component measurement working electrode 5.

That is, in this biosensor 2, the blood component measurement counter electrode (an example of the second electrode) 6 and the blood component measurement working electrode (an example of the first electrode) 5 are arranged sequentially from the blood supply port 13 side.

The cover 11 of the biosensor 2 has an air hole 14 formed therein for promoting the capillary phenomenon when a drop of blood is applied to the blood supply port 13 and for allowing the blood to permeate to a part over the blood component measurement working electrode 5 of the blood component measurement counter electrode 6 (the part of the reagent 9 farther away from the blood supply port 13).

Next, the configuration of the biosensor 2 is described in further details.

In the present invention, the material of the insulating substrate 4 is not particularly limited. Examples thereof that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer cast nylon (MC), polybutylene terephthalate (PBT), methacrylic resin (PMMA), ABS resin (ABS), and glass Among them, polyethylene terephthalate (PET), polycarbonate (PC), and polyimide (PI) are preferable and polyethylene terephthalate (PET) is more preferable.

Furthermore, the size of the insulating substrate 4 is not particularly limited. It has, for example, a total length of 5 to 100 mm, a width of 2 to 50 mm, and a thickness of 0.05 to 2 mm, preferably a total length of 7 to 50 mm, a width of 3 to 20 mm, and a thickness of 0.1 to 1 mm, and further preferably a total length of 10 to 30 mm, a width of 3 to 10 mm, and a thickness of 0.1 to 0.6 mm.

Each electrode arranged on the insulating substrate 4 can be formed by using, for example, gold, platinum, or palladium as a material, forming a conductive layer by a sputtering method or a vapor deposition method, and then processing it into a specific electrode pattern with a laser. Examples of the laser that can be used include a YAG laser, a $CO_2$ laser, and an excimer laser. The electrode pattern is not limited to those disclosed in the present invention and it can be any electrode pattern as long as it allows the effects of the present invention to be obtained. The electrodes of the biosensor 2 that is used in the present invention may be coated with a polymeric material for the purposes of, for example, preventing impurities from adhering to them and preventing them from being oxidized. The surfaces of the electrodes can be coated as follows. For example, a solution of a polymeric material is prepared and this is dropped or applied onto the electrode surfaces, which then is dried. Examples of the drying method include natural drying, air drying, hot air drying, and heat drying.

The electron carrier of the biosensor 2 to be used is not particularly limited. Examples thereof include ferricyanide, p-benzoquinone, p-benzoquinone derivatives, phenazine methosulfate, methylene blue, ferrocene, and ferrocene derivatives. The amount of the electron carrier to be mixed is not particularly limited but is, for example, 0.1 to 1000 mM, preferably 1 to 500 mM, and more preferably 10 to 200 mM per measurement or per biosensor.

In the present invention, examples of the biological information include a glucose value, a lactic acid value, a uric acid level, a bilirubin level, and a cholesterol level. The oxidoreductase to be used in the present invention may be selected suitably depending on the type of the biological information. Examples of the oxidoreductase include glucose oxidase, lactate oxidase, cholesterol oxidase, bilirubin oxidase, glucose dehydrogenase, and lactate dehydrogenase. The amount of the oxidoreductase is, for example, 0.01 to 100 U, preferably 0.05 to 10 U, and more preferably 0.1 to 5 U per sensor or per measurement. Among them, the glucose value is preferable as the biological information, and in this case, oxidoreductase is preferably glucose oxidase or glucose dehydrogenase.

In the present invention, the reagent 9 can be formed as follows. For example, 0.1 to 5.0 U/sensor of flavin adenosine dinucleotide dependent glucose dehydrogenase (FAD-GDH), 10 to 200 mM of potassium ferricyanide, 1 to 50 mM of maltitol, and 20 to 200 mM of taurine are added to 0.01 to 2.0 wt % carboxymethyl cellulose (CMC) solution to be dissolved therein and thereby a reagent solution is prepared. This is dropped onto the electrodes of the insulating substrate 4 and then is dried.

Next, in the present invention, the material of the spacer 10 is not particularly limited but, for example, a similar material to that of the insulating substrate 4 can be used. Furthermore, the size of the spacer 10 is not particularly limited but the spacer 10 has, for example, a total length of 5 to 100 mm, a width of 2 to 50 mm, and a thickness of 0.01 to 1 mm, preferably a total length of 7 to 50 mm, a width of 3 to 20 mm, and a thickness of 0.05 to 0.5 mm, and more preferably a total length of 10 to 30 mm, a width of 3 to 10 mm, and a thickness of 0.05 to 0.25 mm. The spacer 10 has an I-shaped cut part formed to serve as the blood supply path 12 for introducing blood. It also is possible to implement the present invention by, for example, forming the cut part of the blood supply path 12 in a T-shape and thereby suitably providing reagent portions and electrode parts for the respective ends of the blood supply path so that the hematocrit measurement and the glucose measurement can be carried out separately.

Furthermore, in the present invention, the material of the cover 11 is not particularly limited but, for example, a similar material to that of the insulating substrate 4 can be used. It is further preferable that the portion corresponding to the ceiling portion of the blood supply path 12 of the cover 11 be subjected to a hydrophilic treatment. Examples of the method used for the hydrophilic treatment include a method in which a surfactant is applied and a method in which a hydrophilic functional group such as a hydroxyl group, a carbonyl group, or a carboxyl group is introduced into the cover 11 surface by, for example, a plasma treatment. The size of the cover 11 is not particularly limited but the cover 11 has, for example, a total length of 5 to 100 mm, a width of 3 to 50 mm, and a thickness of 0.01 to 0.5 mm, preferably a total length of 10 to 50 mm, a width of 3 to 20 mm, and a thickness of 0.05 to 0.25 mm, and more preferably a total length of 15 to 30 mm, a width of 5 to 10 mm, and a thickness of 0.05 to 0.1 mm. Preferably, an air hole 14 is formed in the cover 11. The shape thereof is, for example, round, oval, or polygonal. The air hole 14 has, for example, a maximum diameter of 0.01 to 10 mm, preferably a maximum diameter of 0.05 to 5 mm, and more preferably a maximum diameter of 0.1 to 2 mm. The air hole 14 may be formed by, for example, making a hole with a laser or a drill, or may be formed using a mold that allows an air vent part to be formed when the cover 11 is formed. Next, as shown in FIG. 2, the biosensor 2 can be produced by stacking the insulating substrate 4, the spacer 10, and the cover 11 in this order and forming them into one body. In forming them into one body, the aforementioned three members may be attached together with an adhesive or may be heat-sealed. Examples of the adhesive that can be used include an epoxy adhesive, an acrylic adhesive, a polyurethane adhesive, a thermosetting adhesive (such as a hot-melt adhesive), and a UV curable adhesive.

Returning to FIG. 1 to continue the description, a voltage applying unit 15 for applying a voltage and a current-voltage conversion part 16 are connected, through a switching circuit 17, to the input terminal portion 7 of the biological information measurement device according to the first embodiment of the present invention.

Specifically, an application voltage part 18 of the voltage applying unit 15 is connected to the switching circuit 17, the input terminal portion 7, the blood component measurement working electrode 5, the reagent 9, and the blood component measurement counter electrode 6 of the biosensor 2, and a reference voltage part 19 of the voltage applying unit 15.

For example, when the voltage of the application voltage part 18 is 300 mV and the voltage of the reference voltage part 19 is 200 mV, a voltage of 100 mV is applied between the blood component measurement working electrode 5 and the blood component measurement counter electrode 6.

In the present embodiment, the voltage of the reference voltage part 19 is fixed while the voltage of the application voltage part 18 is changed, thus obtaining voltage waveforms described later.

The reference voltage part 19 is provided to reduce the effect caused by the noise of the voltage supplied from a power supply unit 20.

In any case, the current caused by the difference in voltage between the blood component measurement working electrode 5 and the blood component measurement counter electrode 6 flows between the blood component measurement working electrode 5 and the blood component measurement counter electrode 6, and the current flowing therebetween is converted to voltage, which is carried out by a current-voltage conversion part (for example, a resistor provided between the blood component measurement counter electrode 6 and the reference voltage part 19) 16 in FIG. 1.

A voltage is applied to the voltage applying unit 15 through a control unit 21. This voltage is applied, for a predetermined duration, to the blood component measurement working electrode 5 and the blood component measurement counter electrode 6 of the biosensor 2 through the input terminal portion 7. By this voltage application, the current that flows between the electrodes in the biosensor 2 is converted to a voltage in the current-voltage conversion part 16. After that, the voltage is digitally converted in an A/D conversion part 22 and the voltage thus digitally converted is compared to a threshold value by a determination means 23.

In a display unit 24 connected to the control unit 21, a glucose value detected in the biosensor 2 and a determination result provided by the determination means 23 are displayed.

The power supply unit 20 shown in FIG. 1 is used for supplying power to the respective parts described above.

Furthermore, numeral 25 indicates a memory unit that is provided with a calibration curve and a calibration table that are prepared beforehand from ambient temperature and tables including, for example, the application voltage and the application time employed in measuring hematocrit values and glucose.

Furthermore, a clock 26 is connected to the control unit 21, and the control unit 21 is configured to make use of the time of the clock 26 to execute various control operations.

Moreover, a correction means 27 is provided in the control unit 21. It corrects the measured blood glucose level in consideration of the hematocrit value and effects of various interfering substances and thereby improves the accuracy of measuring the blood glucose level.

Figure 3A:
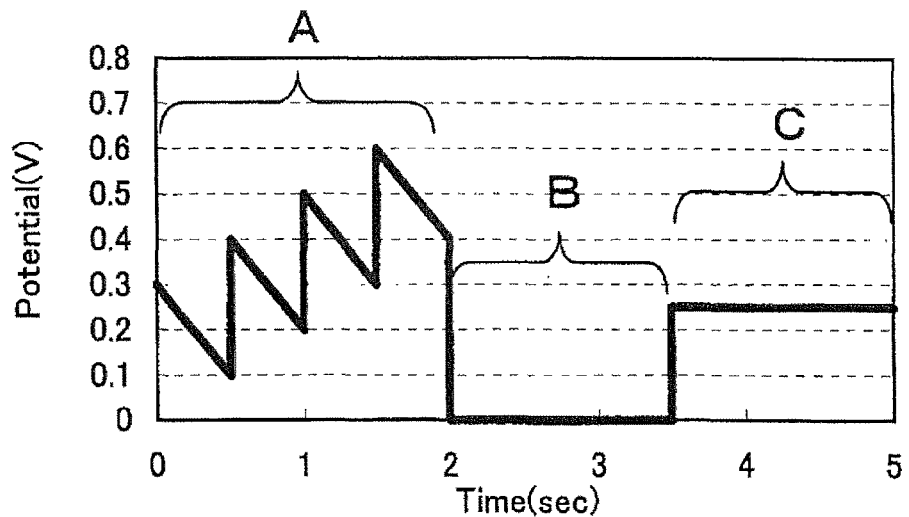
FIG. 3A is a diagram showing a waveform of a voltage that is applied over time in the biological information measurement device according to First Embodiment of the present invention.

The present embodiment is characterized in that the control unit 21 is allowed to execute each of a voltage sweep mode A, a voltage application stop mode B, and a biological information measurement mode C shown in FIG. 3A. FIG. 3A is a diagram showing a waveform of the voltage that is applied over time in the biological information measurement device according to First Embodiment of the present invention.

In First Embodiment, a voltage is applied, in the voltage sweep mode A, to the first input terminal (not shown in the drawings) and the second input terminal (not shown in the drawings) of the input terminal portion 7, that is, a first input terminal (not shown in the drawings) of the blood component measurement working electrode 5 and the blood component measurement counter electrode 6 (not shown in the drawings), while the voltage is swept from a low potential to a high potential.

In First Embodiment, after the above-mentioned voltage sweep mode A, the voltage application stop mode B stops the application of the voltage to the first input terminal (not shown in the drawings) of the input terminal portion 7 and the second input terminal (not shown in the drawings) of the input terminal portion 7, that is, the blood component measurement working electrode 5 and the blood component measurement counter electrode 6.

In First Embodiment, after the above-mentioned voltage application stop mode B, the biological information measurement mode C applies a voltage to the first input terminal (not shown in the drawings) of the input terminal portion 7 and the second input terminal (not shown in the drawings) of the input terminal portion 7, that is, the blood component measurement working electrode 5 and the blood component measurement counter electrode 6, and thereby biological information (a glucose value) is measured.

Figure 3B:
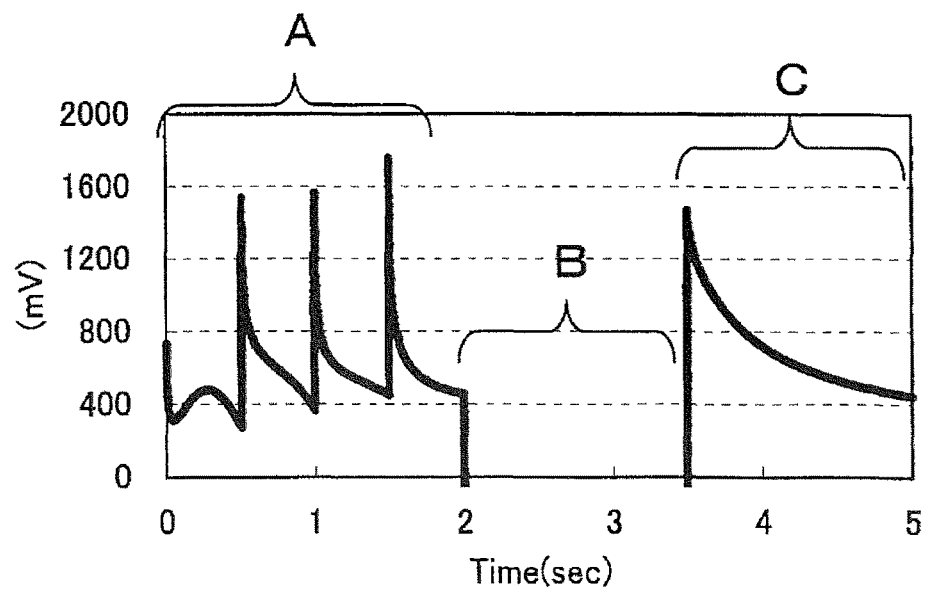
FIG. 3B is a diagram showing a waveform of a current over time in the biological information measurement device according to First Embodiment of the present invention.
Figure 4:
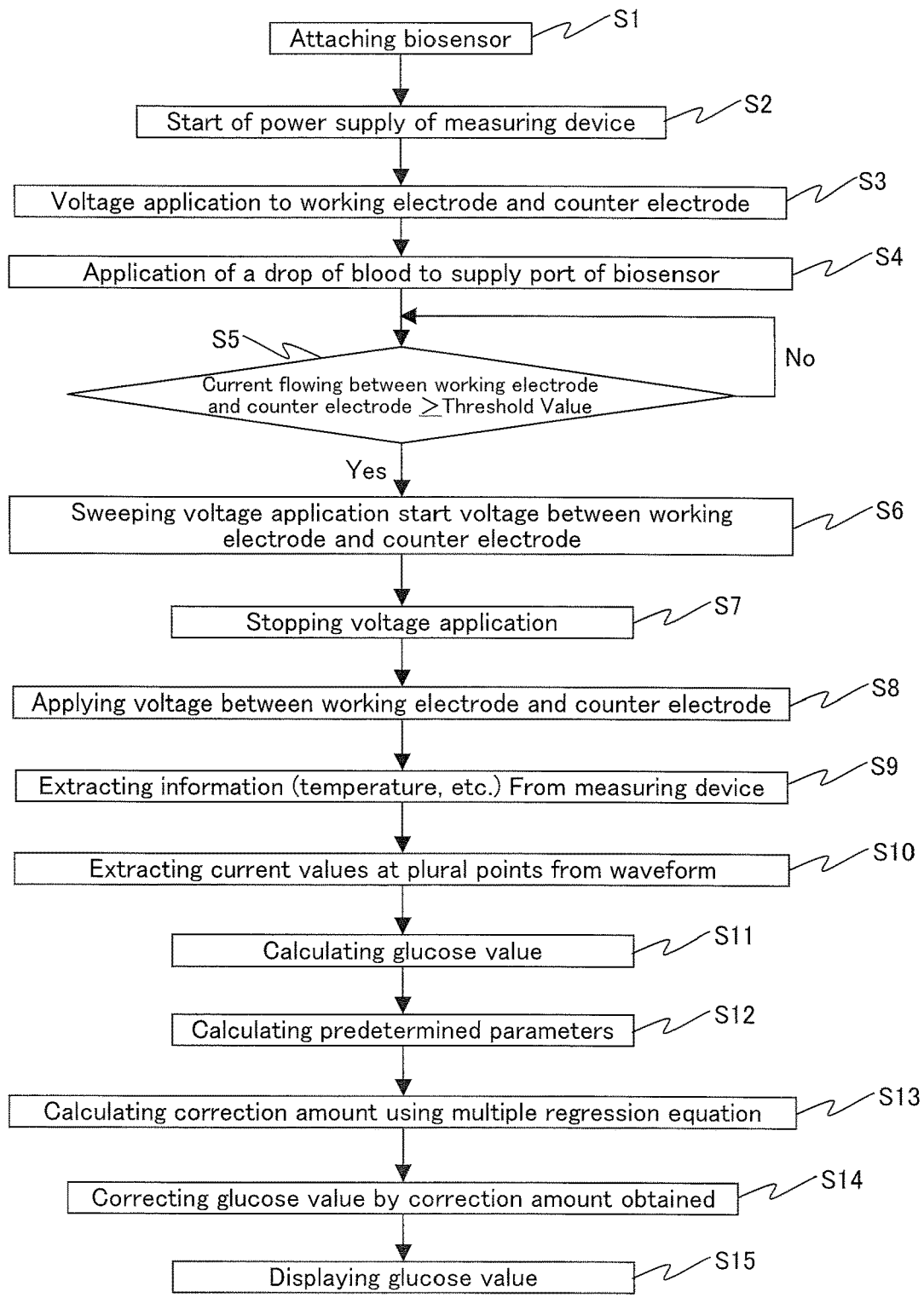
FIG. 4 is an operation flow chart for the biological information measurement device according to First Embodiment of the present invention.

Next, using FIGS. 2 to 4, the measurement flow in the voltage sweep mode A, the voltage application stop mode B, and the biological information measurement mode C is described in further details. FIG. 4 is an operation flow chart for the biological information measurement device according to First Embodiment of the present invention.

First, the biosensor 2 shown in FIG. 2, which is stored in plurality inside a drying container (not shown in the drawings) before being used, is taken out one by one from the drying container whenever the glucose value (the blood glucose level, biological information) is measured, and one end of the biosensor 2 is inserted into the insertion opening 3 as shown in FIG. 1 (S1 "Attaching Biosensor" shown in FIG. 4) and thereby the biosensor 2 is electrically connected to the input terminal portion 7. As a result, the control unit 21 recognizes that the biosensor 2 has been attached to the input terminal portion 7 and then allows the measurement operation to start (S2 "Start of Power Supply of Measuring Device" shown in FIG. 4).

In this state, no drop of blood of a user has been applied to the blood supply port 13 part.

Upon starting the measurement operation, the control unit 21 allows an application voltage to be supplied to each of the blood component measurement working electrode 5 and the blood component measurement counter electrode 6 of the biosensor 2 through the voltage applying unit 15 and the input terminal portion 7 (S3 "Voltage Application to Working Electrode and Counter Electrode" shown in FIG. 4).

In First Embodiment, the application voltage that is supplied between the blood component measurement working electrode 5 and the blood component measurement counter electrode 6 is, for example, 0.5 V.

Next, the user exudes blood by pricking, for example, a finger with a lancet or the like and a drop of the blood is applied to the blood supply port 13 of the biosensor 2 (S4 "Application of A Drop of Blood to Supply Port of Biosensor" shown in FIG. 4).

Then, a current starts flowing between the blood component measurement working electrode 5 and the blood component measurement counter electrode 6, the current is converted to a voltage in the current-voltage conversion part 16, which thereafter is subjected to A/D conversion in the A/D conversion part 22, and then determination is carried out by the determination means 23 of the control unit 21.

Specifically, the control unit 21 measures the value of the current flowing between the blood component measurement working electrode 5 and the blood component measurement counter electrode 6 and compares the voltage value proportional to the current value with a predetermined threshold value (for example, 10 mV). When the voltage value is equal to or higher than the threshold value (S5 "Current flowing between Measurement Working Electrode and Measurement Counter Electrode ≥ Threshold Value" shown in FIG. 4), the voltage of the voltage applying unit 15 is swept in a serrated profile as in the voltage sweep mode A shown in FIG. 3 (S6

"Sweeping Voltage Application Start Voltage between Working Electrode and Counter Electrode" shown in FIG. 4).

Next, as shown in FIG. 3, in the voltage application stop mode B, voltage application is stopped (S7 "Stopping Voltage Application" shown in FIG. 4). Thereafter, in the biological information measurement mode C, a voltage is applied between the blood component measurement working electrode 5 and the blood component measurement counter electrode 6 (S8 "Applying Voltage between Working Electrode and Counter Electrode" shown in FIG. 4).

Then, the control unit 21 extracts temperature information from a temperature sensor (not shown in the drawings) (S9 "Extracting Information (Temperature, etc.) from Measuring Device" shown in FIG. 4).

Furthermore, in the voltage sweep mode A, the voltage application stop mode B, and the biological information measurement mode C, current values measured at a plurality of predetermined times are extracted (S10 "Extracting Current Values at Plural Points from Waveform" shown in FIG. 4).

That is, FIG. 3B shows the waveform of the current flowing between the blood component measurement working electrode 5 and the blood component measurement counter electrode 6, and the current values measured at a plurality of predetermined times in the current waveform are extracted.

After an application time of 1.5 seconds has elapsed, the control unit 21 calculates the glucose value (biological information) (S11 "Calculating Glucose Value" shown in FIG. 4).

Next, a plurality of parameters (x1, x2, x3, ..., x10) are calculated based on the current values measured at a plurality of predetermined times, which were extracted above, the temperature information of the biological information measurement device, which was extracted above, and the like (S12 "Calculating Predetermined Parameters" shown in FIG. 4). Then, the correction amount is calculated using a multiple regression equation (for example, Formula 1 below) (S13 "Calculating Correction Amount Using Multiple Regression Equation" shown in FIG. 4).

$$y = ax1 + bx2 + cx3 \ldots + kx10 + 1 \quad \text{(Formula 1)}$$

(wherein y denotes a correction amount, x1, x2, x3, ..., x10 denote parameters, and a, b, c, ... 1 denote coefficients).

Furthermore, the glucose value calculated above at S11 shown in FIG. 4 is corrected by the correction amount y described above (S14 "Correcting Glucose Value by Correction Amount Obtained" shown in FIG. 4).

Then, the glucose value determined, with the correction having been carried out as described above, is displayed on the display unit 24 as the final glucose value (blood glucose level) (S15 "Displaying Glucose Value" shown in FIG. 4).

The characteristic point in the present embodiment is that in the voltage sweep mode A shown in FIG. 3A, the voltage to be applied between the blood component measurement working electrode 5 and the blood component measurement counter electrode 6 was changed to have a serrated profile.

Specifically, as shown in FIG. 3A, the voltage was first reduced linearly from 0.3 V to 0.1 V between 0 and 0.5 second, then reduced linearly from 0.4 V to 0.2 V between 0.5 and 1.0 second, further reduced linearly from 0.5 V to 0.3 V between 1.0 and 1.5 seconds, and then reduced linearly from 0.6 V to 0.4 V between 1.5 and 2.0 seconds.

Depending on the reagent composition, etc., the application voltage is not limited to this but desirably, it is changed to have a serrated profile in a potential width including the oxidation potential of the electron carrier contained in the reagent.

As a result, the current flowing between the blood component measurement working electrode 5 and the blood component measurement counter electrode 6 in the voltage sweep mode A has a current waveform with at least three sharp points as shown in FIG. 3B. FIG. 3B is a diagram showing a waveform of a current over time in the biological information measurement device according to First Embodiment of the present invention.

In FIG. 3B, the current waveform with the sharp points in this case corresponds to the timings when the above-mentioned voltage applied between the blood component measurement working electrode 5 and the blood component measurement counter electrode 6 is increased sharply after being reduced (0.5 second, 1.0 second, and 1.5 seconds).

In the present embodiment, at S10 shown in FIG. 4, current values are extracted at a plurality of points during the voltage sweep mode A and the biological information measurement mode C shown in FIG. 3B.

Specifically, current values are extracted at 0.5, 0.6, 0.8, 1.0, 1.1, 1.3, 1.5, 1.6, 2.0, 3.6, and 5.0 seconds in FIG. 3B.

At S12 shown in FIG. 4, predetermined parameters are calculated from the above-mentioned current values extracted (for example, a parameter x1 is one obtained by dividing the current value obtained at 5.0 seconds by the current value obtained at 0.5 second) and using these parameters, a correction amount is calculated using a multiple regression equation at S13 shown in FIG. 4. Then, the glucose value calculated at S11 shown in FIG. 4 is corrected by the correction amount obtained at S13 shown in FIG. 4 and finally the glucose value is displayed on the display unit 24 at S15 shown in FIG. 4.

In the present embodiment, the glucose value (biological information) displayed on the display unit 24 tends not to be affected by the individual differences, storage conditions of the biosensor 2, variation in the temperature of the biosensor reaction part, technique of applying a drop of blood, etc.

That is, the biological information measurement device of the present embodiment can reduce the occurrence of variation in the glucose value (biological information) caused by the effects of the individual differences, storage conditions of the biosensor 2, variation in the temperature of the biosensor reaction part, technique of applying a drop of blood, etc.

The reason why such occurrence of variation can be reduced is described below.

Figure 5:
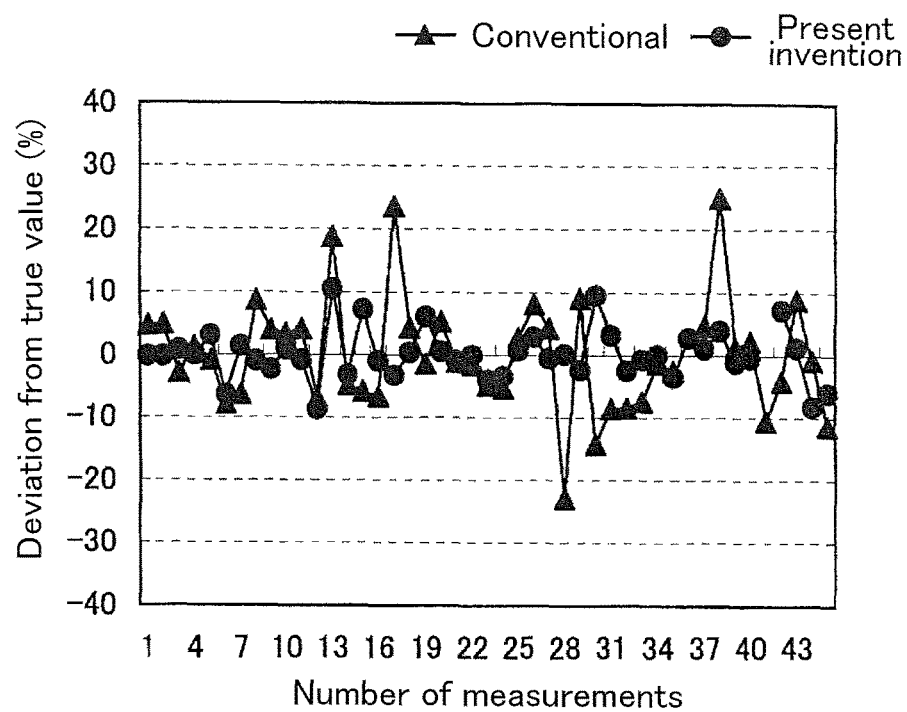
FIG. 5 is a diagram showing variations in biological information after correction obtained by the biological information measurement device according to First Embodiment of the present invention and a conventional biological information measurement device.

FIG. 5 shows how the glucose value measured varies depending on hematocrit in the blood.

FIG. 5 shows variations after correction in a conventional product and the embodiment of the present invention.

Specifically, FIG. 5 shows that by what percentage the glucose values (corrected) deviated from the glucose value (true value), with the glucose values (corrected) being calculated using nine types of blood prepared by shifting the levels of the glucose value and the hematocrit value.

As a result, as shown in FIG. 5, the standard deviation caused in a commercially available common conventional example was 9.06% while the standard deviation caused in the present embodiment was only 4.05%, resulting in a rate of reduction in variation of 55.27%.

The reason why the variation was able to be reduced considerably is because in the present embodiment, as described above, the voltage of the voltage applying unit 15 is swept in a serrated profile as in the voltage sweep mode A shown in FIG. 3A, which makes it easier to extract the value that depends on the hematocrit value, then parameters are calculated from the above-mentioned current values obtained at a plurality of points, a correction amount is calculated using a multiple regression equation, and the glucose value measured is corrected by the correction amount.

Figure 6:
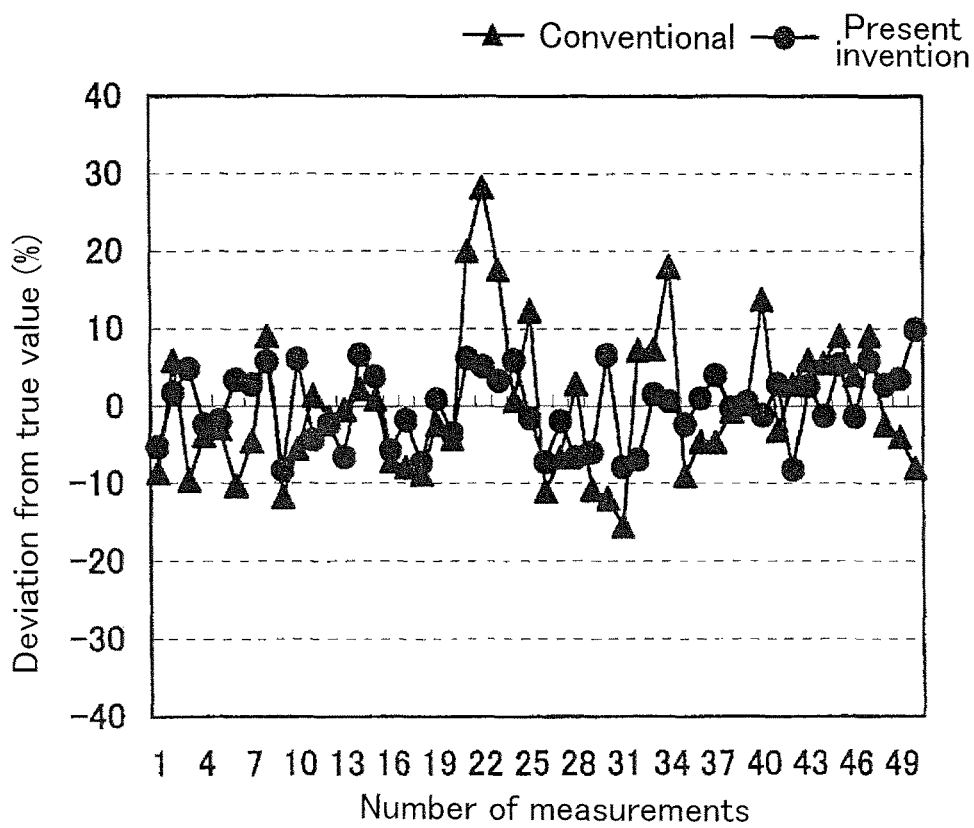
FIG. 6 is a diagram showing variations in biological information after correction obtained by the biological information measurement device according to First Embodiment of the present invention and a conventional biological information measurement device.

FIG. 6 shows that by what percentage the glucose values (corrected) deviated from the glucose value (true value), with the glucose values (corrected) being calculated using ten types of blood in which two types of reducing substances that were different in oxidation potential were added and the levels of glucose value were shifted.

As a result, as shown in FIG. 6, the standard deviation caused in a commercially available common conventional example was 9.31% while the standard deviation caused in the present embodiment was only 4.84%, resulting in a rate of reduction in variation of 48.02%.

The reason why the variation was able to be reduced considerably is because in the present embodiment, as described above, the voltage of the voltage applying unit 15 is swept in a serrated profile as in the voltage sweep mode A shown in FIG. 3A, which makes it easier to extract the value that depends on the reducing substance, then parameters are calculated from the above-mentioned current values obtained at a plurality of points, a correction amount is calculated using a multiple regression equation, and the glucose value measured is corrected by the correction amount.

Figure 7:
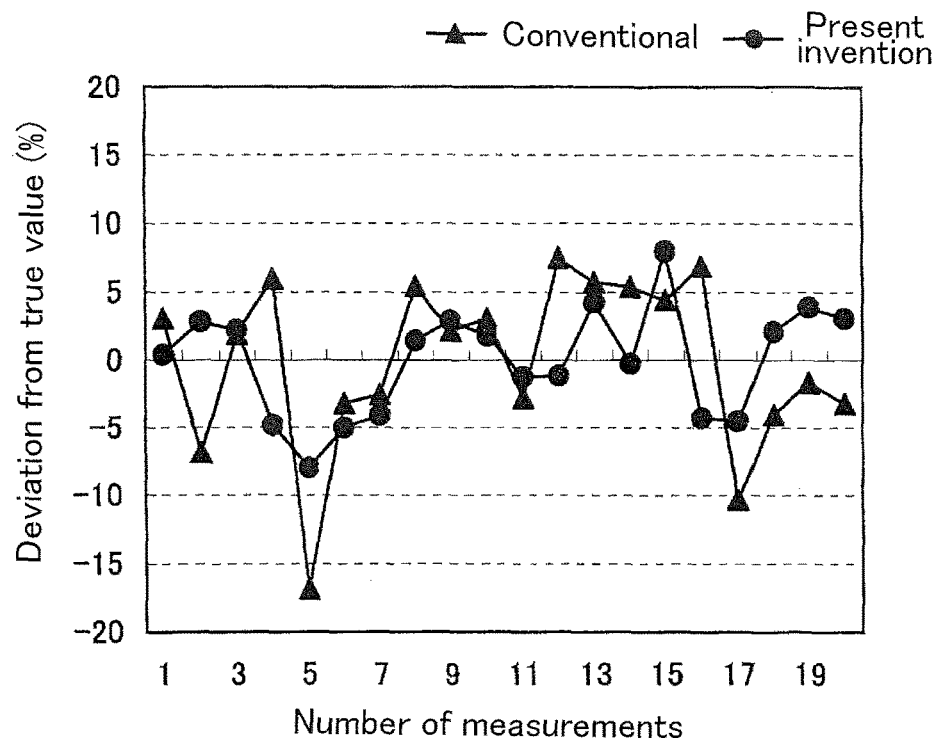
FIG. 7 is a diagram showing variation between individuals in biological information after correction obtained by the biological information measurement device according to First Embodiment of the present invention.

FIG. 7 shows the effect of individual differences.

That is, FIG. 7 shows that by what percentage the glucose values (corrected) each deviated from the glucose value (true value), with the glucose values (corrected) being measured using blood (whose components were unadjusted) of 20 people.

As a result, as shown in FIG. 7, the standard deviation caused in a commercially available common conventional example was 6.37% while the standard deviation caused in the present embodiment was only 4.01%, resulting in a rate of reduction in variation of 36.96%.

The reason why the variation was able to be reduced considerably is because in the present embodiment, as described above, the voltage of the voltage applying unit 15 is swept in a serrated profile as in the voltage sweep mode A shown in FIG. 3A, which makes it easier to extract the value that depends on the individual differences, then parameters are calculated from the above-mentioned current values obtained at a plurality of points, a correction amount is calculated using a multiple regression equation, and the glucose value measured is corrected by the correction amount.

In this case, the blood actually used was different from the blood of FIGS. 6 and 7 whose components had been adjusted, and except for the glucose value, the components thereof were not determined. However, the reduction tendency in the amount of variation was able to be fully verified.

Figure 8:
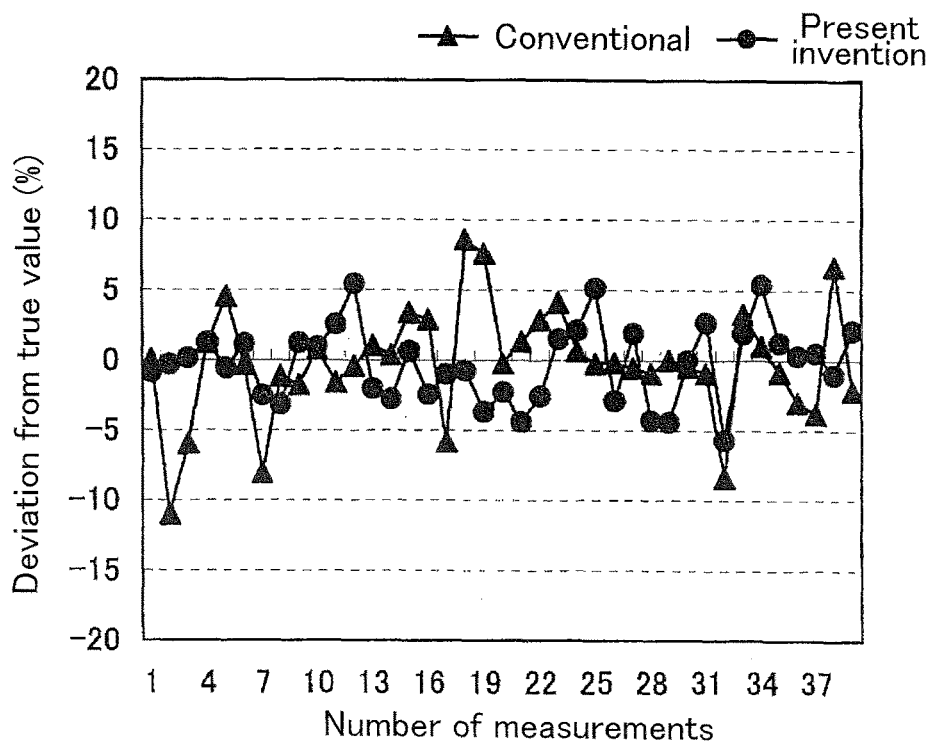
FIG. 8 is a diagram showing the effects of exposure on variation in biological information after correction obtained by the biological information measurement device according to First Embodiment of the present invention.

FIG. 8 shows the effect of exposure of the biosensor 2.

In this case, the glucose value was measured using the biosensor 2 and blood with shifted levels of glucose values. The biosensor 2 used herein was, for example, one that had been allowed to stand at a temperature of 30° C. and a humidity of 80% for five hours, one that had been allowed to stand at a temperature of 40° C. and a humidity of 80% for two hours, and one that had been allowed to stand at a temperature of 30° C. and a humidity of 80% for two hours and successively at a temperature of 40° C. and a humidity of 80% for three hours.

As a result, as shown in FIG. 8, the standard deviation caused in a commercially available common conventional example was 4.05% while the standard deviation caused in the present embodiment was only 2.74%, resulting in a rate of reduction in variation of 32.48%.

The reason why the variation was able to be reduced considerably is because in the present embodiment, as described above, the voltage of the voltage applying unit 15 is swept in a serrated profile as in the voltage sweep mode A shown in FIG. 3A, which makes it easier to extract the value that depends on the exposure, then parameters are calculated from the above-mentioned current values obtained at a plurality of points, a correction amount is calculated using a multiple regression equation, and the glucose value measured is corrected by the correction amount.

Figure 9:
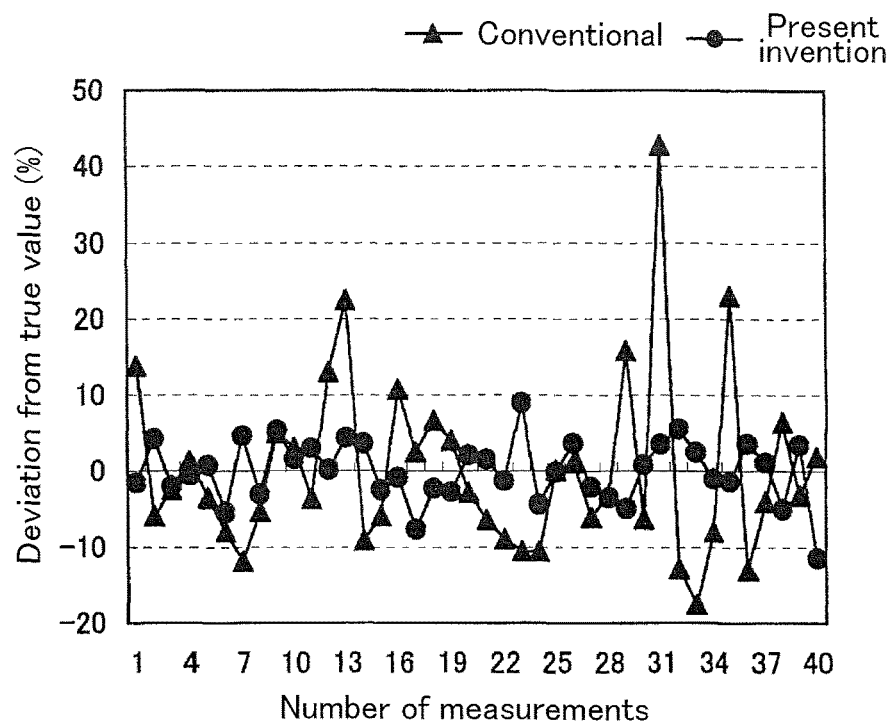
FIG. 9 is a diagram showing the effects of temperature on variation in biological information after correction obtained by the biological information measurement device according to First Embodiment of the present invention.

FIG. 9 shows variation in the temperature of the biosensor reaction part caused by, for example, the temperature of fingers holding the biosensor 2 and the effect of the temperature of blood when it is measured.

In this case, the temperature of the biosensor reaction part was adjusted to 35° C., 33° C., 28° C., and 25° C., while the temperature of blood was adjusted to 35° C. and 25° C.

As a result, as shown in FIG. 9, the standard deviation caused in a commercially available common conventional example was 3.87% while the standard deviation caused in the present embodiment was only 1.76%, resulting in a rate of reduction in variation of 54.59%.

The reason why the variation was able to be reduced considerably is because in the present embodiment, as described above, the voltage of the voltage applying unit 15 is swept in a serrated profile as in the voltage sweep mode A shown in FIG. 3A, which makes it easier to extract the value that depends on the temperature of the biosensor reaction part and the temperature of blood, then parameters are calculated from the above-mentioned current values obtained at a plurality of points, a correction amount is calculated using a multiple regression equation, and the glucose value measured is corrected by the correction amount.

Figure 10:
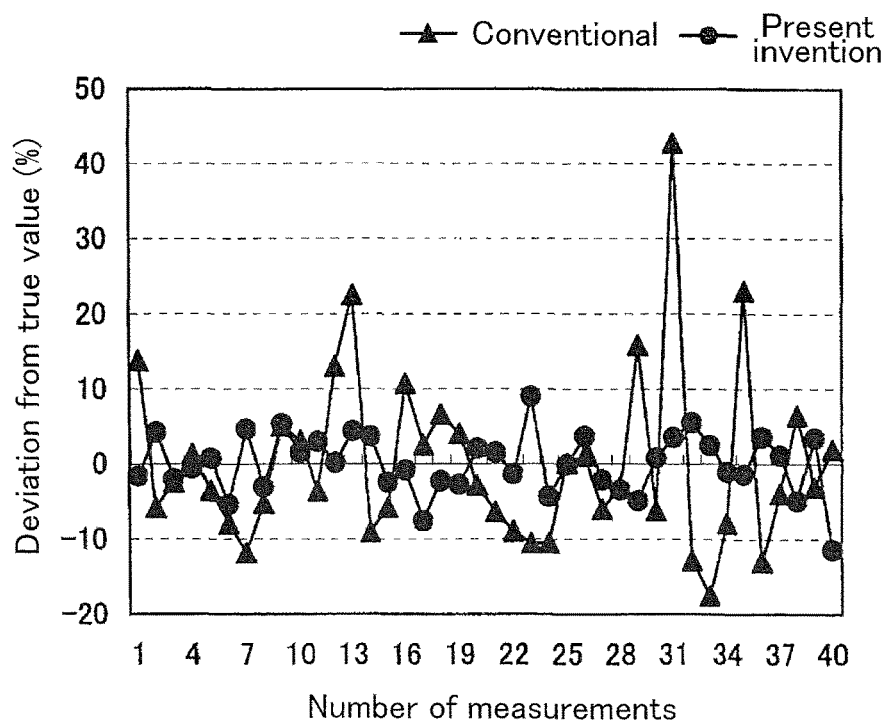
FIG. 10 is a diagram showing the effects of the technique of applying a drop of blood on variation in biological information after correction obtained by the biological information measurement device according to First Embodiment of the present invention.

FIG. 10 shows the effect of the technique of applying a drop of blood to the blood supply port 13 of the biosensor 2.

That is, the method of applying a drop of blood is a method in which a drop of blood whose amount is insufficient for the measurement is applied first and then a sufficient amount of blood for the measurement is added, a method in which a drop of blood is applied over time, with the blood supply port being covered with a finger, or a method in which a drop of blood is applied so that a large amount of blood is provided for the sensor throughout the upper and lower parts thereof.

As a result, as shown in FIG. 10, the standard deviation caused in a commercially available common conventional example was 11.69% while the standard deviation caused in the present embodiment was only 4.03%, resulting in a rate of reduction in variation of 65.51%.

The reason why the variation was able to be reduced considerably is because in the present embodiment, as described above, the voltage of the voltage applying unit 15 is swept in a serrated profile as in the voltage sweep mode A shown in FIG. 3A, which makes it easier to extract the value that depends on the method of applying a drop of blood, then parameters are calculated from the above-mentioned current values obtained at a plurality of points, a correction amount is calculated using a multiple regression equation, and the glucose value measured is corrected by the correction amount.

With the above results, it was described that the effects of, for example, the individual differences, storage conditions of the biosensor 2, variation in the temperature of the biosensor reaction part, and technique of applying a drop of blood were remedied. A multiple regression equation may be determined from parameters correlated to respective factors and the glucose value calculated may be corrected multiple times by each correction amount obtained with respect to each factor as in this case or the glucose value calculated may be corrected at once by a correction amount obtained with respect to the degree of the effects of all the error factors added up. In either way, good results are obtained.

<Embodiment 2>

Figure 11A:
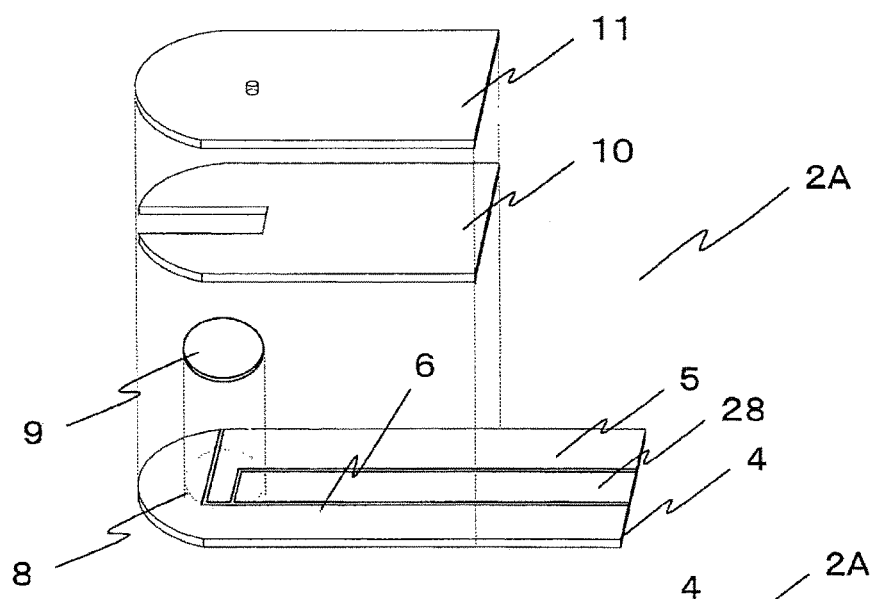
FIG. 11A is an exploded perspective view of a biosensor that is used for a biological information measurement device according to Second Embodiment of the present invention.
Figure 11B:
FIG. 11B is a side view of the biosensor that is used for the biological information measurement device according to Second Embodiment of the present invention.
Figure 11C:
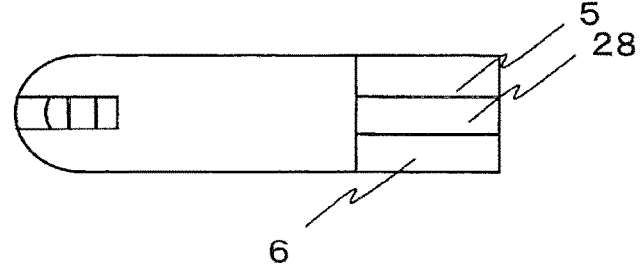
FIG. 11C is a plan view of the biosensor that is used for the biological information measurement device according to Second Embodiment of the present invention.
Figure 12:
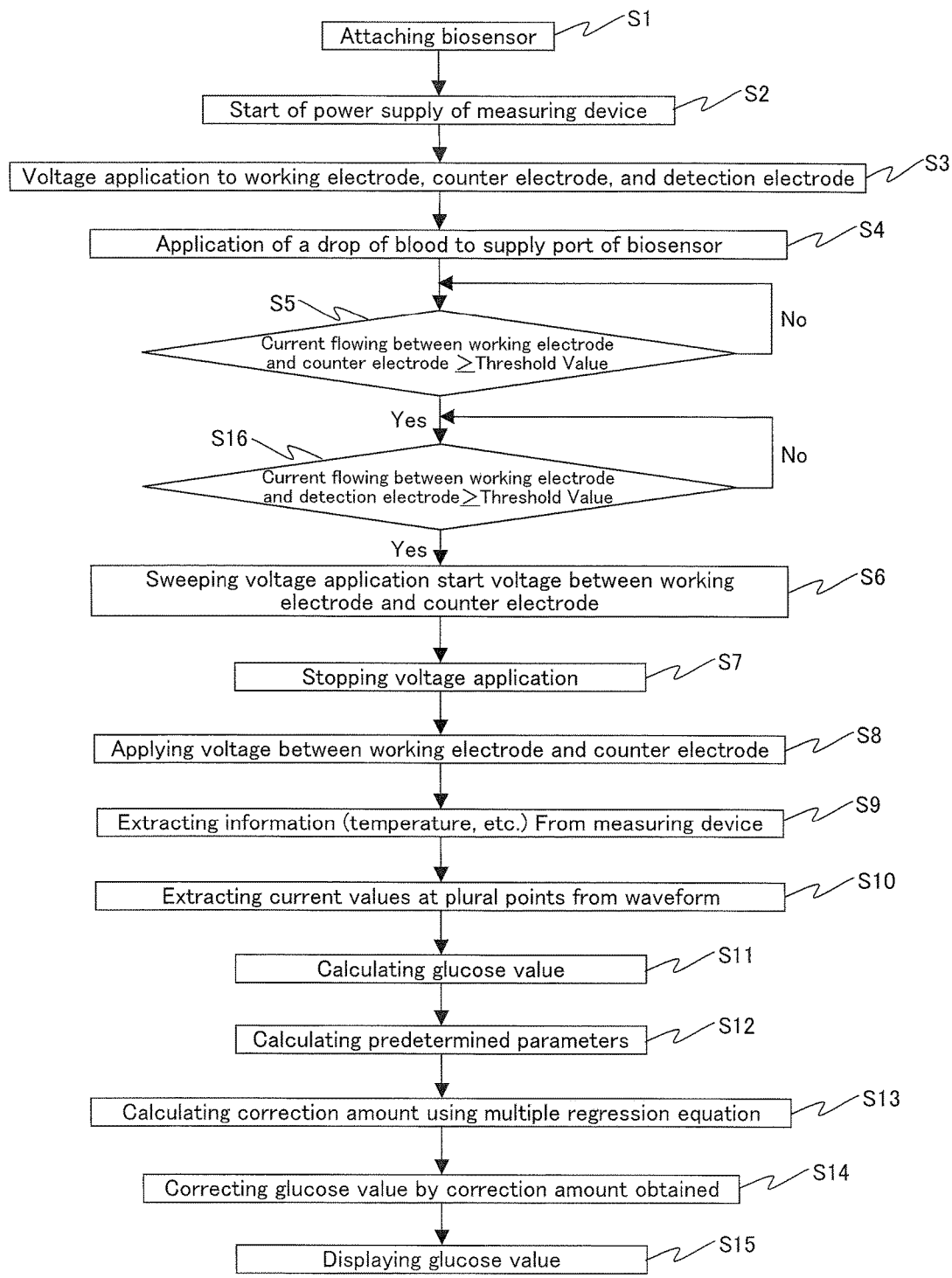
FIG. 12 is an operation flow chart for the biological information measurement device according to Second Embodiment of the present invention.

FIGS. 11 and 12 show Embodiment 2 of the present invention. FIG. 11A is an exploded perspective view of a biosensor that is used for a biological information measurement device according to Second Embodiment of the present invention. FIG. 11B is a side view of the biosensor that is used for the biological information measurement device according to Second Embodiment of the present invention. FIG. 11C is a plan view of the biosensor that is used for the biological information measurement device according to Second Embodiment of the present invention. FIG. 12 is an operation flow chart for the biological information measurement device according to Second Embodiment of the present invention. In Embodiment 2, a blood component introduction detection electrode (an example of a third electrode) 28 was provided on an insulating substrate 4.

That is, as shown in FIG. 11A, the biosensor 2 is formed, with three electrode, i.e., a blood component measurement working electrode (an example of the first electrode) 5, a blood component measurement counter electrode (an example of the second electrode) 6, and the blood component introduction detection electrode 28, being arranged, on a rectangular-shaped insulating substrate 4, opposed to one another at predetermined intervals.

Parts of the blood component measurement working electrode 5, the blood component measurement counter electrode 6, and the blood component introduction detection electrode 28 that are located on one end side (the right end side in FIG. 2) of the insulating substrate 4 are inserted into the body case 1 through the insertion opening 3 shown in FIG. 1 to come into contact with the input terminal portion 7 and thereby they are electrically connected to the biological information measurement device.

Furthermore, as shown in FIG. 2, a reagent portion 8 is disposed among the blood component measurement working electrode 5, the blood component measurement counter electrode 6, and the blood component introduction detection electrode 28 on the other side of the biosensor 2A (on the opposite side to the portion to be inserted into the insertion opening 3).

In this biosensor 2A, a reagent 9 is placed on the reagent portion 8. With this state, the blood component measurement working electrode 5, the blood component measurement counter electrode 6, and the blood component introduction detection electrode 28 are connected to one another through the reagent 9 placed on the reagent portion 8. The reagent 9 has a composition containing oxidoreductase, such as glucose dehydrogenase, and a mediator and selectively containing, as optional components, a polymeric material, an enzyme stabilizer, a crystal homogenizer, etc.

Furthermore, a cover 11 is placed above the insulating substrate 4 and the reagent 9, with a spacer 10 being interposed therebetween. On one end side (on the right end side in FIG. 2) of the insulating substrate 4, parts of the blood component measurement working electrode 5, the blood component measurement counter electrode 6, and the blood component introduction detection electrode 28 are exposed without being covered by the spacer 10 and the cover 11.

The exposed parts of the blood component measurement working electrode 5, the blood component measurement counter electrode 6, and the blood component introduction detection electrode 28 are electrically connected to the input terminal portion 7 as described above.

In the spacer 10 of the biosensor 2A, a blood supply path 12 for introducing blood is formed. This blood supply path 12 extends from the other end side (the left end side in FIG. 2) of the biosensor 2A to above the reagent 9, and the other end side that is open to the outside forms a blood supply port 13.

As described above, the blood component measurement working electrode 5, the blood component measurement counter electrode 6, and the blood component introduction detection electrode 28 are electrically connected to the input terminal portion 7. Specifically, the blood component measurement working electrode 5 is connected to a first input terminal (not shown in the drawings) of the input terminal portion 7, the blood component measurement counter electrode 6 is connected to a second input terminal (not shown in the drawings) of the input terminal portion 7, and the blood component introduction detection electrode 28 is connected to a third input terminal (not shown in the drawings) of the input terminal portion 7.

Furthermore, as is understood also from FIG. 11A, in this biosensor 2A, the blood component measurement counter electrode 6 is arranged closest to the blood supply port 13, followed by the blood component measurement working electrode 5 and the blood component introduction detection electrode 28 in this order.

That is, in this biosensor 2A, the blood component measurement counter electrode (an example of the second electrode) 6, the blood component measurement working electrode (an example of the first electrode) 5, and the blood component introduction detection electrode (an example of the third electrode) 28 are arranged sequentially from the blood supply port 13 side.

The cover 11 of the biosensor 2A has an air hole 14 formed therein for promoting the capillary phenomenon when a drop of blood is applied to the blood supply port 13 and for allowing the blood to permeate to a part (the part of the reagent 9 farther away from the blood supply port 13), of the blood component measurement counter electrode 6, reaching the blood component introduction detection electrode 28 over the blood component measurement working electrode 5.

Next, using FIGS. 11 and 12, the measurement flow in the voltage sweep mode A, the voltage application stop mode B, and the biological information measurement mode C is described in further details. Regarding the same parts as those used in Embodiment 1 above, however, FIGS. 1 to 3 are used. FIG. 12 is an operation flow chart for the biological information measurement device according to Second Embodiment of the present invention.

First, the biosensor 2A shown in FIG. 11, which is stored in plurality inside a drying container (not shown in the drawings) before being used, is taken out one by one from the drying container whenever the glucose value (the blood glucose level, biological information) is measured, and one end of the biosensor 2A is inserted into the insertion opening 3 as shown in FIG. 1 (S1 "Attaching Biosensor" shown in FIG. 12) and thereby the biosensor 2A is electrically connected to the input terminal portion 7. As a result, the control unit 21 recognizes that the biosensor 2A has been attached to the input terminal portion 7 and then allows the measurement operation to start (S2 "Start of Power Supply of Measuring Device" shown in FIG. 12).

In this state, no drop of blood of a user has been applied to the blood supply port 13 part.

Upon starting the measurement operation, the control unit 21 allows an application voltage to be supplied to each of the blood component measurement working electrode 5, the blood component measurement counter electrode 6, and the blood component introduction detection electrode 28 of the biosensor 2A through the voltage applying unit 15 and the input terminal portion 7 (S3 "Voltage Application to Working Electrode, Counter Electrode, and Detection Electrode" shown in FIG. 12).

The application voltage that is supplied between the blood component measurement working electrode 5 and the blood component measurement counter electrode 6 is, for example, 0.5 V.

Next, the user exudes blood by pricking, for example, a finger with a lancet or the like and a drop of the blood is applied to the blood supply port 13 of the biosensor 2A (S4 "Application of A Drop of Blood to Supply Port of Biosensor" shown in FIG. 12).

Then, a current starts flowing between the blood component measurement working electrode 5 and the blood component measurement counter electrode 6, the current is converted to a voltage in the current-voltage conversion part 16, which thereafter is subjected to A/D conversion in the A/D conversion part 22, and then determination is carried out by the determination means 23 of the control unit 21.

Specifically, the control unit 21 measures the value of the current flowing between the blood component measurement working electrode 5 and the blood component measurement counter electrode 6, compares the voltage value proportional to the current value with a predetermined threshold value (for example, 10 mV), and detects that the voltage value is equal to or higher than the threshold value (S5 "Current flowing between Working Electrode and Counter Electrode ≥Threshold Value" shown in FIG. 12).

The control unit 21 measures the value of the current flowing between the blood component measurement working electrode 5 and the blood component measurement counter electrode 6 and compares the voltage value proportional to the current value with a predetermined threshold value (for example, 10 mV). When the control unit 21 detects that the voltage value is equal to or higher than the threshold value, it switches, with a switching circuit 17, from detecting the current flowing between the blood component measurement working electrode 5 and the blood component measurement counter electrode 6 to detecting the current flowing between the blood component measurement working electrode 5 and the blood component introduction detection electrode 28.

Then, after this switching, the control unit 21 measures the value of the current flowing between the blood component measurement working electrode 5 and the blood component introduction detection electrode 28, compares the voltage value proportional to the current value with a predetermined threshold value (for example, 10 mV), and detects that the voltage value is equal to or higher than the threshold value (S16 "Current flowing between Working Electrode and Detection Electrode ≥Threshold Value" shown in FIG. 12). Thereafter, the voltage of the voltage applying unit 15 is swept in a serrated profile as in the voltage sweep mode A shown in FIG. 3 (S6 "Sweeping Voltage Application Start Voltage between Working Electrode and Counter Electrode" shown in FIG. 12").

Next, as shown in FIG. 3, in the voltage application stop mode B, voltage application is stopped (S7 "Stopping Voltage Application" shown in FIG. 12). Thereafter, in the biological information measurement mode C, a voltage is applied between the blood component measurement working electrode 5 and the blood component measurement counter electrode 6 (S8 "Applying Voltage between Working Electrode and Counter Electrode" shown in FIG. 12).

Then, the control unit 21 extracts temperature information from a temperature sensor (not shown in the drawings) (S9 "Extracting Information (Temperature, etc.) from Measuring Device" as shown in FIG. 12).

Furthermore, in the voltage sweep mode A, the voltage application stop mode B, and the biological information measurement mode C, current values measured at a plurality of predetermined times are extracted (S10 "Extracting Current Values at Plural Points from Waveform" as shown in FIG. 12).

That is, FIG. 3B shows the waveform of the current flowing between the blood component measurement working electrode 5 and the blood component measurement counter electrode 6 in the biological information measurement device according to First Embodiment of the present invention, and the current values measured at a plurality of predetermined times in the current waveform are extracted.

After an application time of 1.5 seconds has elapsed, the control unit 21 calculates the glucose value (biological information) (S11 "Calculating Glucose Value" shown in FIG. 12).

Next, a plurality of parameters (×1, ×2, ×3 . . . , ×10) are calculated from the current values measured at a plurality of predetermined times, which were extracted above, the temperature information of the biological information measurement device, which was extracted above, and the like (S12 "Calculating Predetermined Parameters" shown in FIG. 12). Then, the correction amount is calculated using a multiple regression equation (for example, Formula 1 below) (S13 "Calculating Correction Amount Using Multiple Regression Equation" shown in FIG. 12).

$$y = ax1 + bx2 + cx3 \ldots + kx10 + 1 \quad \text{(Formula 1)}$$

(wherein y denotes a correction amount, ×1, ×2, ×3, . . . , ×10 denote parameters, and a, b, c, . . . 1 denote coefficients).

Furthermore, the glucose value calculated above at S11 shown in FIG. 4 is corrected by the correction amount y described above (S14 "Correcting Glucose Value by Correction Amount Obtained" shown in FIG. 12).

Then, the glucose value determined, with the correction having been carried out as described above, is displayed on the display unit 24 as the final glucose value (blood glucose level) (S15 "Display of Glucose Value" shown in FIG. 12).

The characteristic point in the present embodiment is that in the voltage sweep mode A shown in FIG. 3A, the voltage to be applied between the blood component measurement working electrode 5 and the blood component measurement counter electrode 6 was changed to have a serrated profile.

Specifically, as shown in FIG. 3A, the voltage was first reduced linearly from 0.3 V to 0.1 V between 0 and 0.5 second, then reduced linearly from 0.4 V to 0.2 V between 0.5 and 1.0 second, further reduced linearly from 0.5 V to 0.3 V between 1.0 and 1.5 seconds, and then reduced linearly from 0.6 V to 0.4 V between 1.5 and 2.0 seconds.

As a result, the current flowing between the blood component measurement working electrode 5 and the blood component measurement counter electrode 6 in the voltage sweep mode A has a current waveform with at least three sharp points as shown in FIG. 3B.

The current waveform with the sharp points in this case corresponds to the timings when the above-mentioned voltage applied between the blood component measurement working electrode 5 and the blood component measurement counter electrode 6 is increased sharply after being reduced (0.5 second, 1.0 second, and 1.5 seconds).

In the present embodiment, at S10 "Extracting Current Values at Plural Points from Waveform" shown in FIG. 12, current values are extracted at a plurality of points during the voltage sweep mode A and the biological information measurement mode C shown in FIG. 3B.

Specifically, current values are extracted at 0.5, 0.6, 0.8, 1.0, 1.1, 1.3, 1.5, 1.6, 2.0, 3.6, and 5.0 seconds in FIG. 3B.

At S12 "Calculating Predetermined Parameters" shown in FIG. 12, predetermined parameters are calculated from the above-mentioned current values extracted (for example, a parameter x1 is one obtained by dividing the current value obtained at 5.0 seconds by the current value obtained at 0.5 second) and using these parameters, a correction amount is calculated using a multiple regression equation at S13 "Calculating Correction Amount Using Multiple Regression Equation" shown in FIG. 12. Then, the glucose value calculated at S11 "Calculating Glucose Value" shown in FIG. 12 is corrected by the correction amount obtained at S13 "Calculating Correction Amount Using Multiple Regression Equation" shown in FIG. 12 and finally the glucose value is displayed on the display unit 24 at S15 "Displaying Glucose Value" shown in FIG. 12.

<Embodiment 3>

Figure 13:
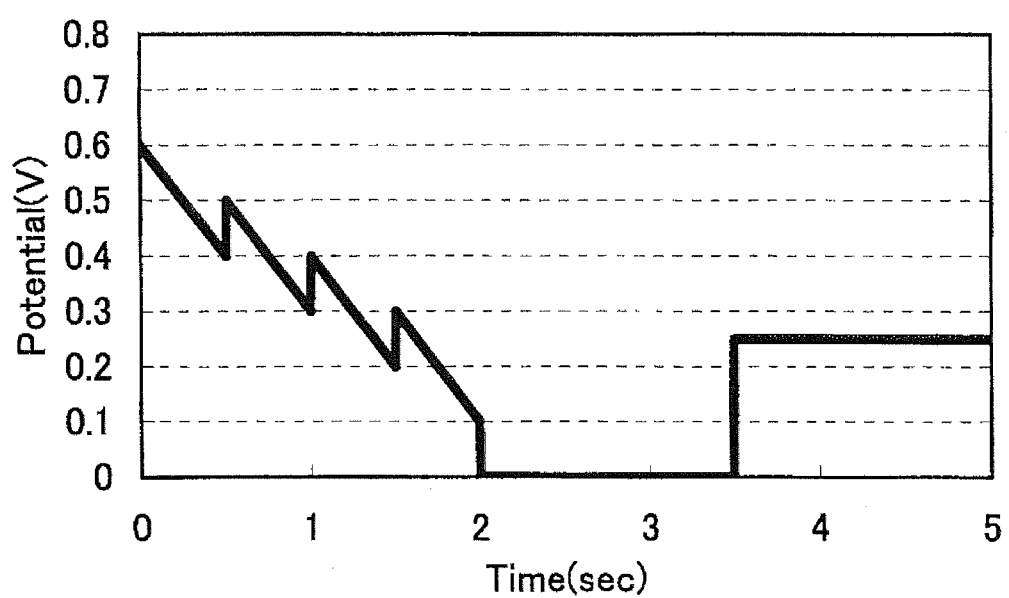
FIG. 13 is a diagram showing a waveform of a voltage that is applied over time in a biological information measurement device according to Third Embodiment of the present invention.

FIG. 13 shows Embodiment 3 of the present invention. In Embodiment 3, the voltage applied between the blood component measurement working electrode 5 and the blood component measurement counter electrode 6 was changed to have a serrated profile by the control unit 21, for example, in the voltage sweep mode A shown in FIG. 3 in the measurement carried out using the biosensor 2 shown in FIG. 2 or the biosensor 2A shown in FIG. 11. That is, FIG. 13 is a diagram showing a waveform of the voltage that is applied over time in a biological information measurement device according to Third Embodiment of the present invention.

Specifically, as shown in FIG. 13, the voltage was first reduced linearly from 0.6 V to 0.4 V between 0 and 0.5 second, then reduced linearly from 0.5 V to 0.3 V between 0.5 and 1.0 second, further reduced linearly from 0.4 V to 0.2 V between 1.0 and 1.5 seconds, and then reduced linearly from 0.3 V to 0.1 V between 1.5 and 2.0 seconds.

<Embodiment 4>

Figure 14A:
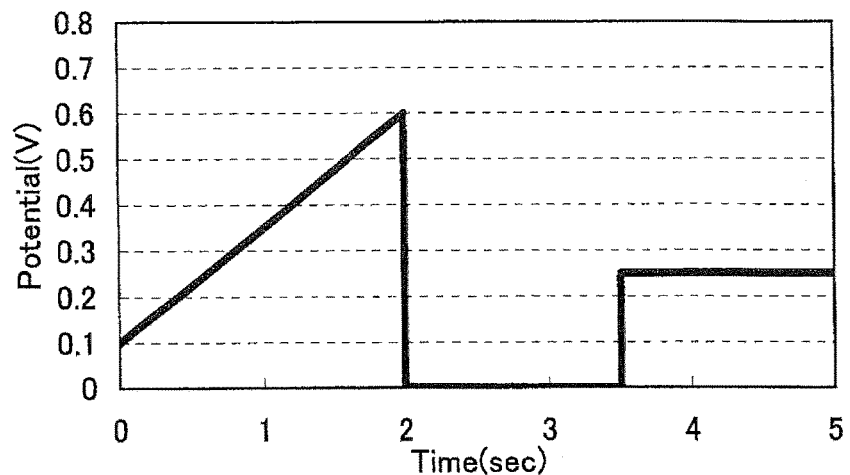
FIG. 14A is a diagram showing a waveform of a voltage that is applied over time in a biological information measurement device according to Fourth Embodiment of the present invention.
Figure 14B:
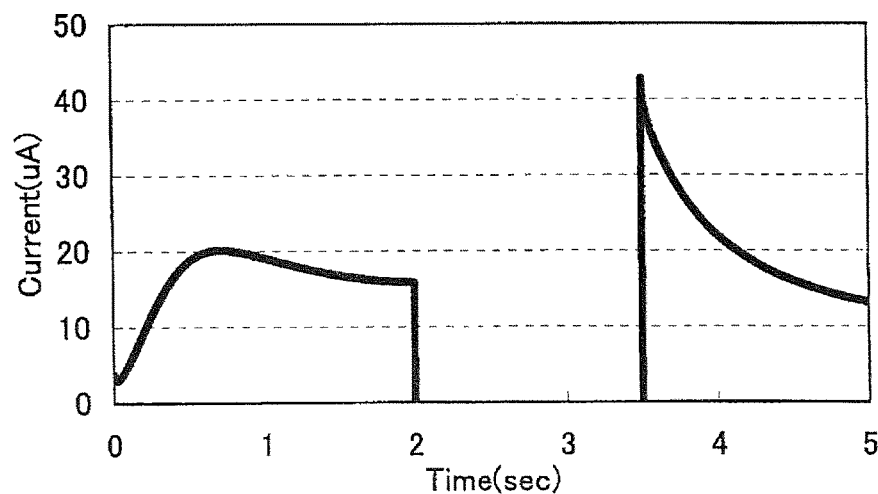
FIG. 14B is a diagram showing a current waveform over time in the biological information measurement device according to Fourth Embodiment of the present invention.

FIG. 14 shows Embodiment 4 of the present invention. In Embodiment 4, the voltage applied between the blood component measurement working electrode 5 and the blood component measurement counter electrode 6 was changed to increase linearly by the control unit 21, for example, in the voltage sweep mode A shown in FIG. 3 in the measurement carried out using the biosensor 2 shown in FIG. 2 or the biosensor 2A shown in FIG. 11. That is, FIG. 14A is a diagram showing a waveform of the voltage that is applied over time in a biological information measurement device according to Fourth Embodiment of the present invention. FIG. 14B is a diagram showing a current waveform over time in the biological information measurement device according to Fourth Embodiment of the present invention.

Specifically, as shown in FIG. 14A, the voltage was first increased linearly from 0.1 V to 0.6 V between 0 and 2.0 seconds.

As a result, as shown in FIG. 14B, in the voltage sweep mode A, the current flowing between the blood component measurement working electrode 5 and the blood component measurement counter electrode 6 increases sharply from 0 to around 0.5 second and then is diverted downward and shows a tendency to decrease gradually from that point in time to 2.0 seconds. This is because the oxidation potential of the electron carrier contained in the reagent falls between 0.1 V and 0.6 V.

In this case, the change caused during the increase of the current is greater than that caused during the decrease.

Then, as shown in FIG. 14B, the current shows a tendency to decrease gradually between 3.5 seconds and 5.0 seconds in the biological information measurement mode C.

<Embodiment 5>

Figure 15A:
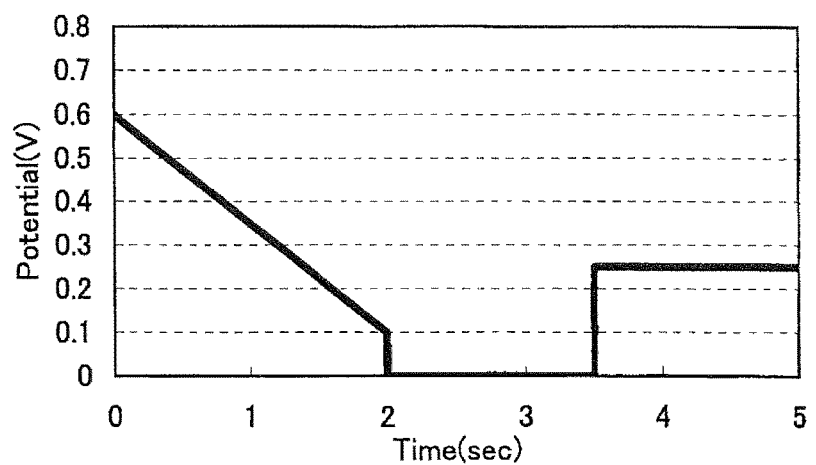
FIG. 15A is a diagram showing a waveform of a voltage that is applied over time in a biological information measurement device according to Fifth Embodiment of the present invention.
Figure 15B:
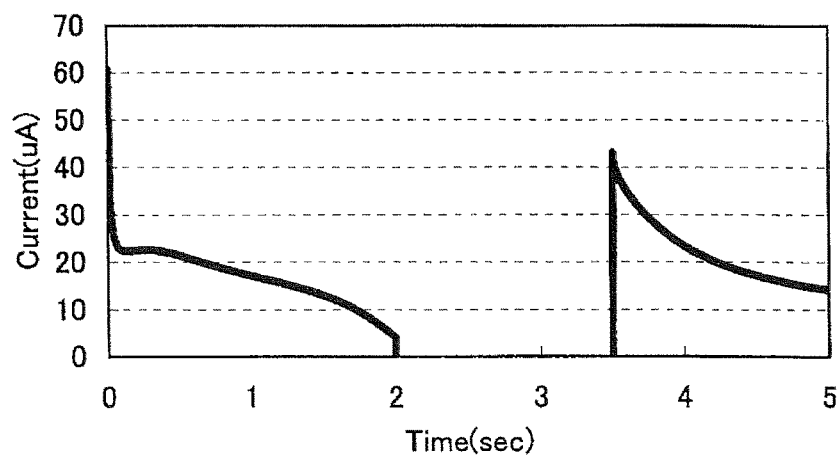
FIG. 15B is a diagram showing a current waveform in the biological information measurement device according to Fifth Embodiment of the present invention.

FIG. 15 shows Embodiment 5 of the present invention. In Embodiment 5, the voltage applied between the blood component measurement working electrode 5 and the blood component measurement counter electrode 6 was changed to decrease linearly by the control unit 21, for example, in the voltage sweep mode A shown in FIG. 3 in the measurement carried out using the biosensor 2 shown in FIG. 2 or the biosensor 2A shown in FIG. 11. That is, FIG. 15A is a diagram showing a waveform of the voltage that is applied over time in a biological information measurement device according to Fifth Embodiment of the present invention. FIG. 15B is a diagram showing a current waveform in the biological information measurement device according to Fifth Embodiment of the present invention.

Specifically, as shown in FIG. 15A, the voltage was first decreased linearly from 0.6 V to 0.1 V between 0 and 2.0 seconds.

As a result, as shown in FIG. 15B, in the voltage sweep mode A, the current flowing between the blood component measurement working electrode 5 and the blood component measurement counter electrode 6 decreases sharply between 0 and around 0.1 second and then shows a tendency to decrease gradually until 2.0 seconds.

In this case, the rate of change of the current obtained until 0.1 second is larger than that obtained after 0.1 second.

Then, as shown in FIG. 15B, the current shows a tendency to decrease gradually from 3.5 seconds to around 5.0 seconds in the biological information measurement mode C.

<Embodiment 6>

Figure 16A:
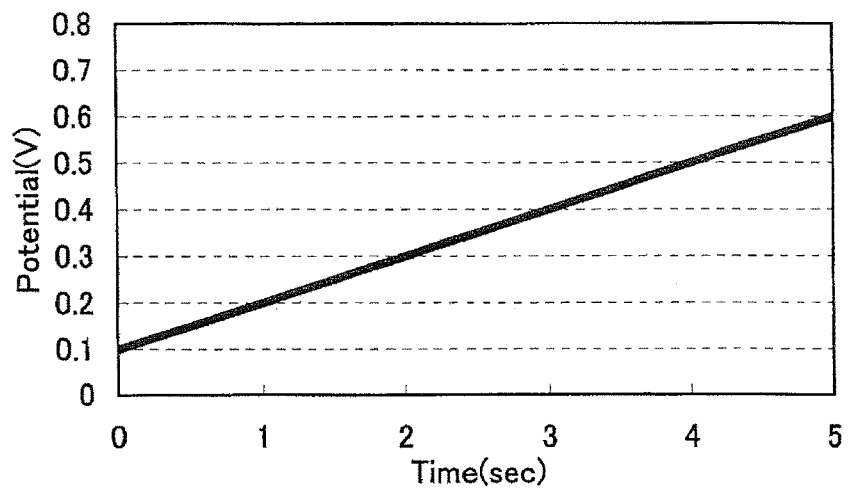
FIG. 16A is a diagram showing a waveform of a voltage that is applied over time in a biological information measurement device according to Sixth Embodiment of the present invention.
Figure 16B:
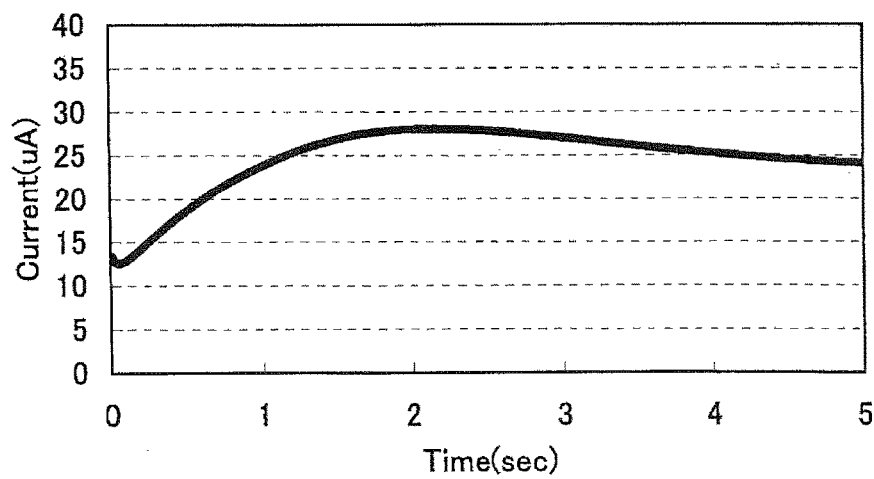
FIG. 16B is a diagram showing a current waveform in the biological information measurement device according to Sixth Embodiment of the present invention.

FIG. 16 shows Embodiment 6 of the present invention. In Embodiment 6, the voltage was continuously increased linearly by the control unit 21, for example, throughout the voltage sweep mode A, the voltage application stop mode B, and the biological information measurement mode C shown in FIG. 3 in the measurement carried out using the biosensor 2 shown in FIG. 2 or the biosensor 2A shown in FIG. 11. That is, FIG. 16A is a diagram showing a waveform of the voltage that is applied over time in a biological information measurement device according to Sixth Embodiment of the present invention. FIG. 16B is a diagram showing a current waveform in the biological information measurement device according to Sixth Embodiment of the present invention.

Specifically, as shown in FIG. 16A, the voltage was increased linearly from 0.1 V to 0.6 V between 0 and 5.0 seconds.

As a result, as shown in FIG. 16B, the current flowing between the blood component measurement working electrode 5 and the blood component measurement counter electrode 6 increases from 0 to around 1.7 seconds and then is diverted downward and shows a tendency to decrease gradually until 5.0 seconds. This is because the oxidation potential of the electron carrier contained in the reagent falls between 0.1 V and 0.6 V.

In this case, the rate of change of the current obtained between 0 and 1.7 seconds is larger than that obtained after 1.7 seconds.

<Embodiment 7>

Figure 17A:
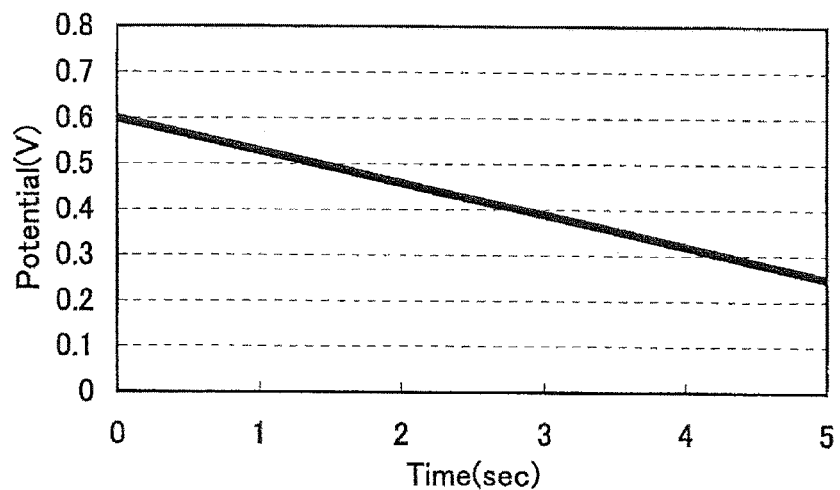
FIG. 17A is a diagram showing a waveform of a voltage that is applied over time in a biological information measurement device according to Seventh Embodiment of the present invention.
Figure 17B:
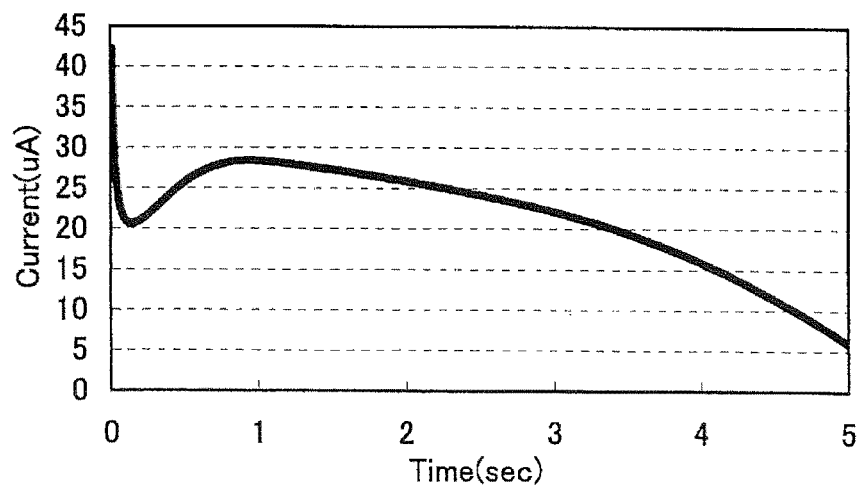
FIG. 17B is a diagram showing a current waveform in the biological information measurement device according to Seventh Embodiment of the present invention.

FIG. 17 shows Embodiment 7 of the present invention. In Embodiment 7, the voltage was continuously decreased linearly by the control unit 21, for example, throughout the voltage sweep mode A, the voltage application stop mode B, and the biological information measurement mode C shown in FIG. 3 in the measurement carried out using the biosensor 2 shown in FIG. 2 or the biosensor 2A shown in FIG. 11. That is, FIG. 17A is a diagram showing a waveform of the voltage that is applied over time in a biological information measurement device according to Seventh Embodiment of the present invention. FIG. 17B is a diagram showing a current waveform in the biological information measurement device according to Seventh Embodiment of the present invention.

Specifically, as shown in FIG. 17A, the voltage was decreased linearly from 0.6 V to 0.2 V between 0 and 5.0 seconds.

As a result, as shown in FIG. 17B, the current flowing between the blood component measurement working electrode 5 and the blood component measurement counter electrode 6 decreases sharply from 0 to around 0.1 second and then is diverted upward and shows a tendency to decrease gradually from 0.7 seconds again.

In this case, the rate of change of the current obtained from 0 to 0.1 second is larger than that obtained after 0.7 second.

<Embodiment 8>

Figure 18:
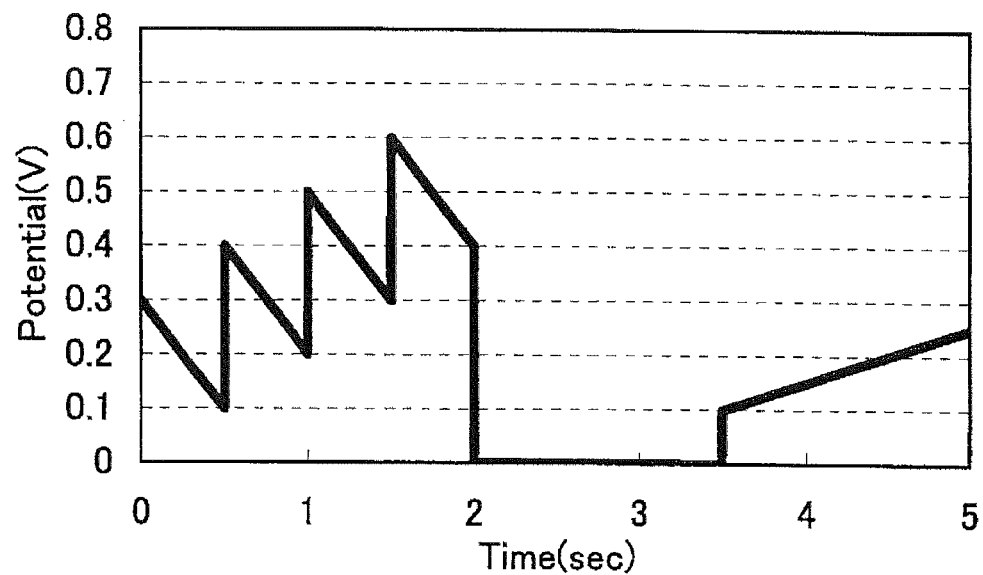
FIG. 18 is a diagram showing a waveform of a voltage that is applied over time in a biological information measurement device according to Eighth Embodiment of the present invention.

FIG. 18 shows Embodiment 8 of the present invention. In Embodiment 8, the voltage applied between the blood component measurement working electrode 5 and the blood component measurement counter electrode 6 was changed to have a serrated profile by the control unit 21, for example, in the voltage sweep mode A shown in FIG. 3 in the measurement carried out using the biosensor 2 shown in FIG. 2 or the biosensor 2A shown in FIG. 11. That is, FIG. 18 is a diagram showing a waveform of the voltage that is applied over time in a biological information measurement device according to Eighth Embodiment of the present invention.

Specifically, as shown in FIG. 18, the voltage is first reduced linearly from 0.3 V to 0.1 V between 0 and 0.5 second, then reduced linearly from 0.4 V to 0.2 V between 0.5 and 1.0 second, further reduced linearly from 0.5 V to 0.3 V between 1.0 and 1.5 seconds, and then reduced linearly from 0.6 V to 0.4 V between 1.5 and 2.0 seconds.

Furthermore, as shown in FIG. 18, after the voltage application stop mode B, the voltage is continuously increased linearly in the biological information measurement mode C.

Specifically, as shown in FIG. 18, the voltage was increased linearly from 0.1 V to 0.25 V between 3.5 and 5.0 seconds, i.e., during the biological information measurement mode C.

<Embodiment 9>

Figure 19:
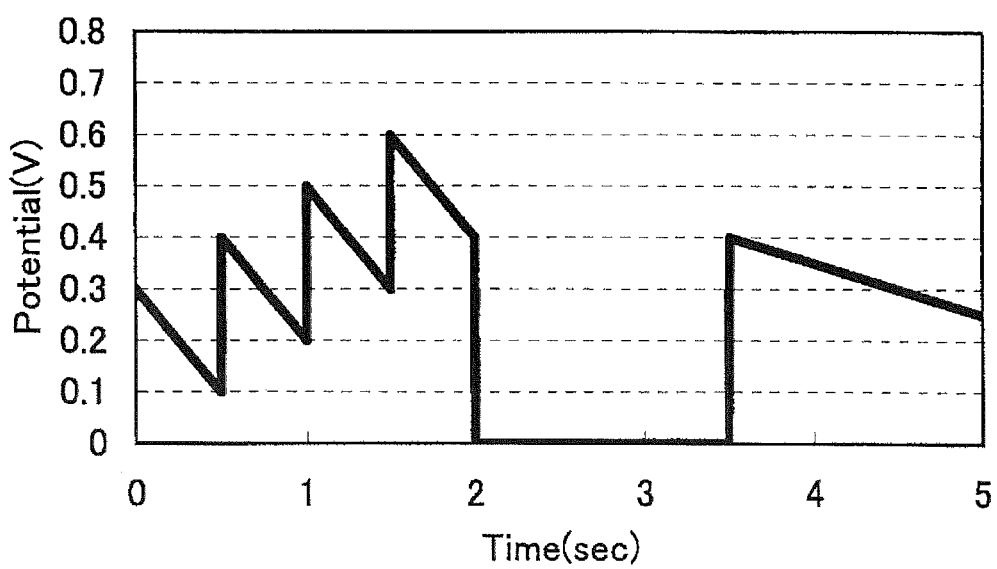
FIG. 19 is a diagram showing a waveform of a voltage that is applied over time in a biological information measurement device according to Ninth Embodiment of the present invention.

FIG. 19 shows Embodiment 9 of the present invention. In Embodiment 9, the voltage applied between the blood component measurement working electrode 5 and the blood component measurement counter electrode 6 was changed to have a serrated profile by the control unit 21, for example, in the voltage sweep mode A shown in FIG. 3 in the measurement carried out using the biosensor 2 shown in FIG. 2 or the biosensor 2A shown in FIG. 11. That is, FIG. 19 is a diagram showing a waveform of the voltage that is applied over time in a biological information measurement device according to Ninth Embodiment of the present invention.

Specifically, as shown in FIG. 19, the voltage is first reduced linearly from 0.3 V to 0.1 V between 0 and 0.5 second, then reduced linearly from 0.4 V to 0.2 V between 0.5 and 1.0 second, further reduced linearly from 0.5 V to 0.3 V between 1.0 and 1.5 seconds, and then reduced linearly from 0.6 V to 0.4 V between 1.5 and 2.0 seconds.

Furthermore, as shown in FIG. 19, after the voltage application stop mode B, the voltage is continuously decreased linearly in the biological information measurement mode C.

Specifically, as shown in FIG. 19, the voltage was decreased linearly from 0.4 V to 0.25 V between 3.5 and 5.0 seconds, i.e., during the biological information measurement mode C.

<Embodiment 10>

Figure 20A:
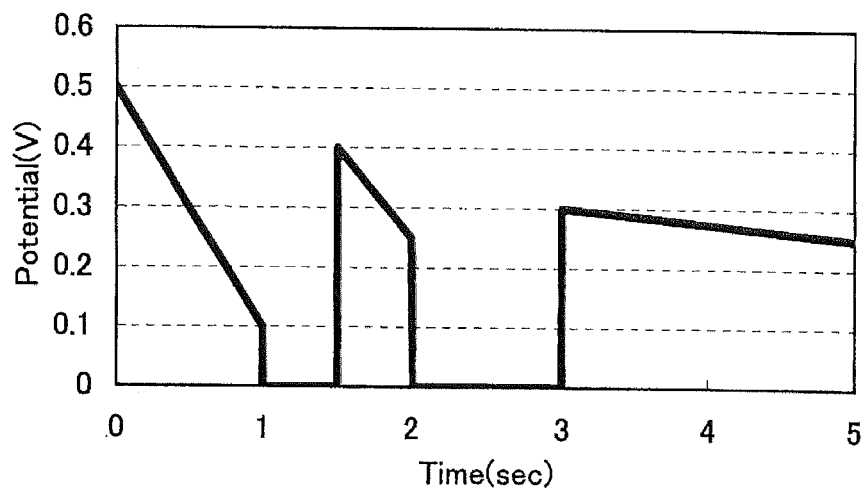
FIG. 20A is a diagram showing a waveform of a voltage that is applied over time in a biological information measurement device according to Tenth Embodiment of the present invention.
Figure 20B:
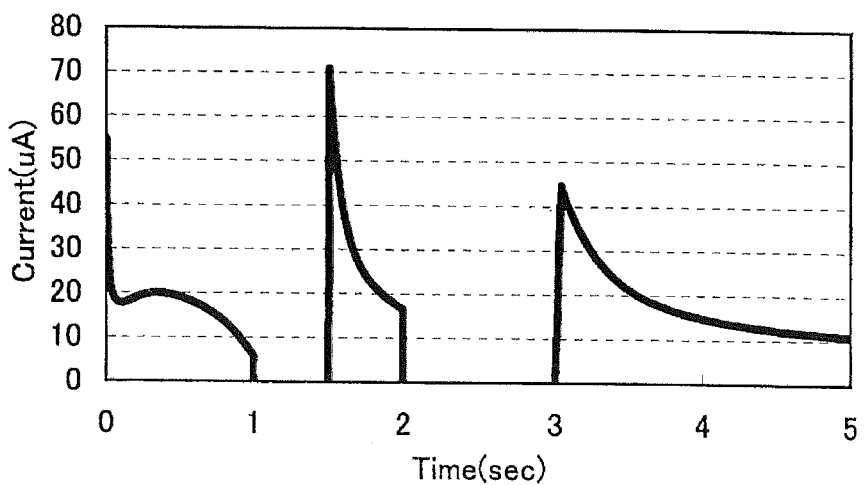
FIG. 20B is a diagram showing a current waveform in the biological information measurement device according to Tenth Embodiment of the present invention.

FIG. 20 shows Embodiment 10 of the present invention. In Embodiment 10, after the voltage is continuously decreased linearly, the voltage application is stopped, and thereafter, the voltage is increased sharply and then is continuously decreased linearly again by the control unit 21, for example, in the voltage sweep mode A shown in FIG. 3 in the measurement carried out using the biosensor 2 shown in FIG. 2 or the biosensor 2A shown in FIG. 11. That is, FIG. 20A is a diagram showing a waveform of the voltage that is applied over time in a biological information measurement device according to Tenth Embodiment of the present invention. FIG. 20B is a diagram showing a current waveform in the biological information measurement device according to Tenth Embodiment of the present invention.

Specifically, as shown in FIG. 20A, the voltage is decreased linearly from 0.5 V to 0.1 V between 0 and 1.0 second in the voltage sweep mode A. Then, as shown in FIG. 20A, the voltage application between the blood component measurement working electrode 5 and the blood component measurement counter electrode 6 is stopped between 1.0 and 1.5 seconds, thereafter, the voltage is increased sharply from 0 V to 0.4 V at the point in time beyond 1.5 seconds, and then the voltage is decreased from 0.4 V to 0.25 V until 2.0 seconds.

As shown in FIG. 20A, the rate of change of the voltage in the first half of the voltage sweep mode A is set to be larger than the rate of change of the voltage in the second half.

Thereafter, as shown in FIG. 20A, after the voltage application stop mode B, the application voltage is decreased gradually from 0.3 V to 0.25 V between 3.0 and 5.0 seconds in the biological information measurement mode C.

As a result, as shown in FIG. 20B, the current flowing between the blood component measurement working electrode 5 and the blood component measurement counter electrode 6 decreases sharply between 0 and 0.1 second, thereafter, it increases gradually until 0.3 second and then is changed to decrease gradually.

Furthermore, as shown in FIG. 20B, the current flowing between the blood component measurement working electrode 5 and the blood component measurement counter electrode 6 increases sharply at 1.5 seconds, and immediately after that it starts decreasing sharply until 2.0 seconds.

Furthermore, as shown in FIG. 20B, the current that increased sharply at 3.0 seconds also decreases gradually between 3.0 and 5.0 seconds in the biological information measurement mode C.

<Embodiment 11>

Figure 21A:
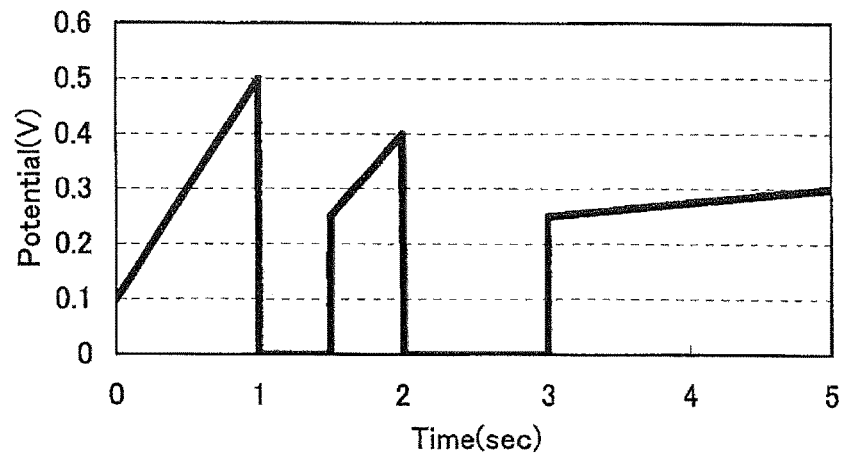
FIG. 21A is a diagram showing a waveform of a voltage that is applied over time in a biological information measurement device according to Eleventh Embodiment of the present invention.
Figure 21B:
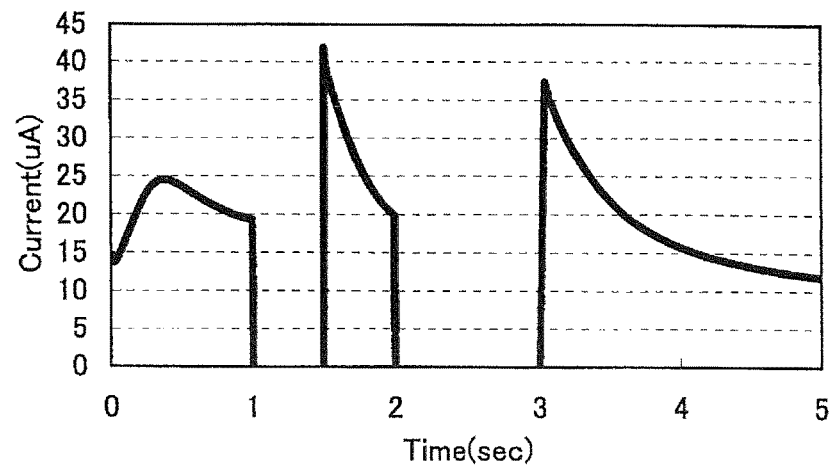
FIG. 21B is a diagram showing a current waveform in the biological information measurement device according to Eleventh Embodiment of the present invention.

FIG. 21 shows Embodiment 11 of the present invention. In Embodiment 11, after the voltage is continuously increased linearly, the voltage application is stopped, and thereafter, the voltage is increased sharply and then is continuously increased linearly again by the control unit 21, for example, in the voltage sweep mode A shown in FIG. 3 in the measurement carried out using the biosensor 2 shown in FIG. 2 or the biosensor 2A shown in FIG. 11. That is, FIG. 21A is a diagram showing a waveform of the voltage that is applied over time in a biological information measurement device according to Eleventh Embodiment of the present invention. FIG. 21B is a diagram showing a current waveform in the biological information measurement device according to Eleventh Embodiment of the present invention.

Specifically, as shown in FIG. 21A, the voltage is increased linearly from 0.1 V to 0.5 V between 0 and 1.0 second in the voltage sweep mode A. Then, as shown in FIG. 21A, the voltage application between the blood component measurement working electrode 5 and the blood component measurement counter electrode 6 is stopped between 1.0 and 1.5 seconds, thereafter, the voltage is increased sharply from 0 V to 0.25 V at the point in time beyond 1.5 seconds, and then the voltage is increased from 0.25 V to 0.4 V until 2.0 seconds.

As shown in FIG. 21A, the rate of change of the voltage in the first half of the voltage sweep mode A is set to be larger than the rate of change of the voltage in the second half.

Thereafter, as shown in FIG. 21A, after the voltage application stop mode B, the application voltage is increased gradually from 0.25 V to 0.3 V between 3.0 and 5.0 seconds in the biological information measurement mode C.

As a result, as shown in FIG. 21B, the current flowing between the blood component measurement working electrode 5 and the blood component measurement counter electrode 6 increases sharply between 0 and 0.3 second, and thereafter, it decreases gradually until 1.0 second.

Furthermore, as shown in FIG. 21B, the current flowing between the blood component measurement working electrode 5 and the blood component measurement counter electrode 6 increases sharply at 1.5 seconds, and immediately after that it starts decreasing sharply until 2.0 seconds.

Furthermore, as shown in FIG. 21B, the current that increased sharply at 3.0 seconds also decreases gradually between 3.0 and 5.0 seconds in the biological information measurement mode C.

<Embodiment 12>

Figure 22A:
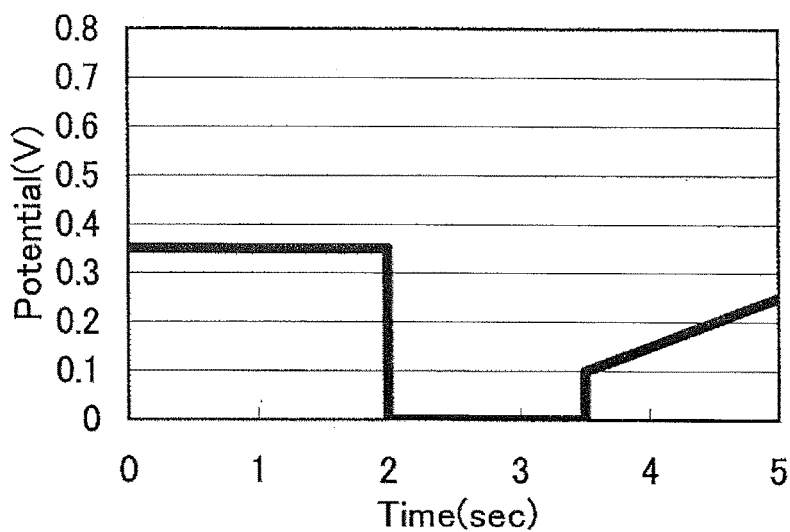
FIG. 22A is a diagram showing a waveform of a voltage that is applied over time in a biological information measurement device according to Twelfth Embodiment of the present invention.
Figure 22B:
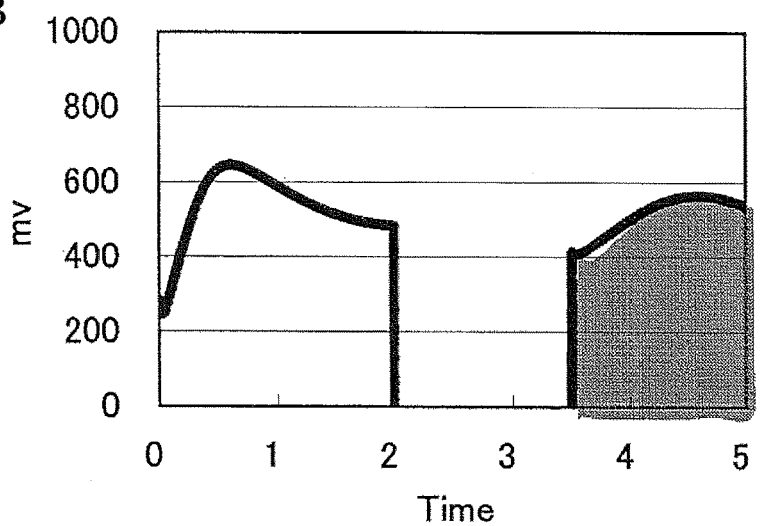
FIG. 22B is a diagram showing a current waveform in the biological information measurement device according to Twelfth Embodiment of the present invention.
Figure 22C:
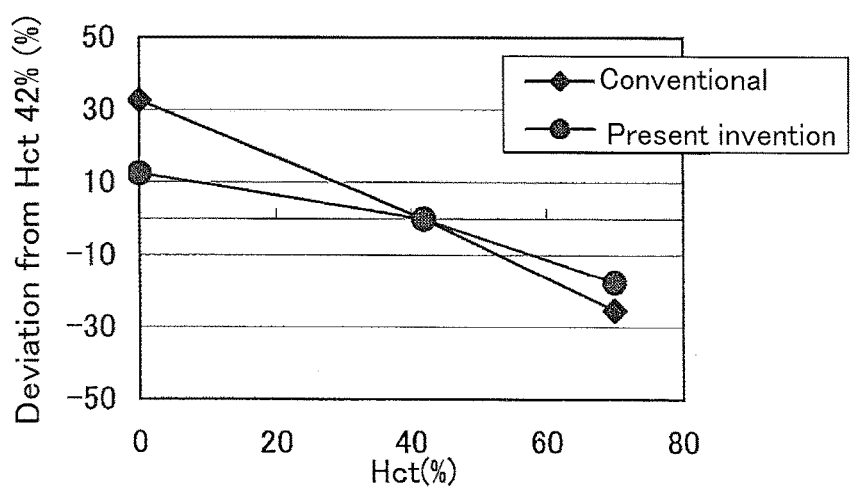
FIG. 22C is a graph showing deviations from a hematocrit value of 42% in biological information measurement devices according to a conventional example and Twenty-Second Embodiment of the present invention.

FIG. 22 shows Embodiment 12 of the present invention. In Embodiment 12, the control unit 21 determines an area from a current value to calculate the biological information value, for example, in the biological information measurement mode C shown in FIG. 3 in the measurement carried out using the biosensor 2 shown in FIG. 2 or the biosensor 2A shown in FIG. 11. That is, FIG. 22A is a diagram showing a waveform of the voltage that is applied over time in a biological information measurement device according to Twelfth Embodiment of the present invention. FIG. 22B is a diagram showing a current waveform in the biological information measurement device according to Twelfth Embodiment of the present invention. FIG. 22C is a graph showing deviations from a hematocrit value of 42% in biological information measurement devices according to a conventional example and Twenty-Second Embodiment of the present invention.

That is, in Embodiment 12, during the biological information measurement mode, with respect to the voltage applying unit, the control unit applies different voltage values between the first input terminal and the second input terminal from the voltage applying unit in a third period and a fourth period of the biological information measurement mode and detects currents flowing between the first input terminal and the second input terminal in the third period and the fourth period, the control unit calculates a current area value from the currents flowing between the first input terminal and the second input terminal in the third period and the fourth period, and the control unit compares the current area value to a standard curve prepared in advance and thereby obtains a biological information measurement value.

Specifically, as shown in FIG. 22A, first, a voltage of 0.35 V is applied between 0 and 2.0 seconds, the voltage application is stopped between 2.0 and 3.5 seconds, and then the voltage is increased linearly from 0.1 to 0.25 V between 3.5 and 5 seconds.

As a result, as shown in FIG. 22B, the current flowing between the blood component measurement working electrode 5 and the blood component measurement counter electrode 6 increases sharply from 0 to 0.5 second and then increases gradually until 2.0 second. Thereafter, similarly between 3.0 and 5.0 seconds in the biological information measurement mode C, the voltage that increased sharply at 3.0 seconds increases gradually.

In Embodiment 12, the area enclosed by the time-current curve obtained in the biological information measurement mode C is considered as a current area value S. This current area value is highly correlated with the amounts of, for example, glucose, lactic acid, uric acid, bilirubin, and cholesterol contained in a biological sample. Then, the control unit compares the current area value S with the standard curve prepared in advance and thereby calculates the glucose value, lactic acid value, uric acid level, bilirubin level, cholesterol level, etc., i.e., the biological information value.

In Embodiment 12, a hematocrit value in a biological sample was obtained as the biological information. As shown in FIG. 22C, with respect to deviations of the hematocrit value obtained by the biological information measurement device of a conventional example and the hematocrit value obtained by the biological information measurement device according to Twelfth Embodiment of the present invention, the deviation in the conventional example was considerably large in the case of a hematocrit value of 42%. On the other hand, in the biological information measurement device according to Twelfth Embodiment of the present invention, the deviation was reduced in the case of a hematocrit value of 42%.

<Embodiment 13>

Figure 23:
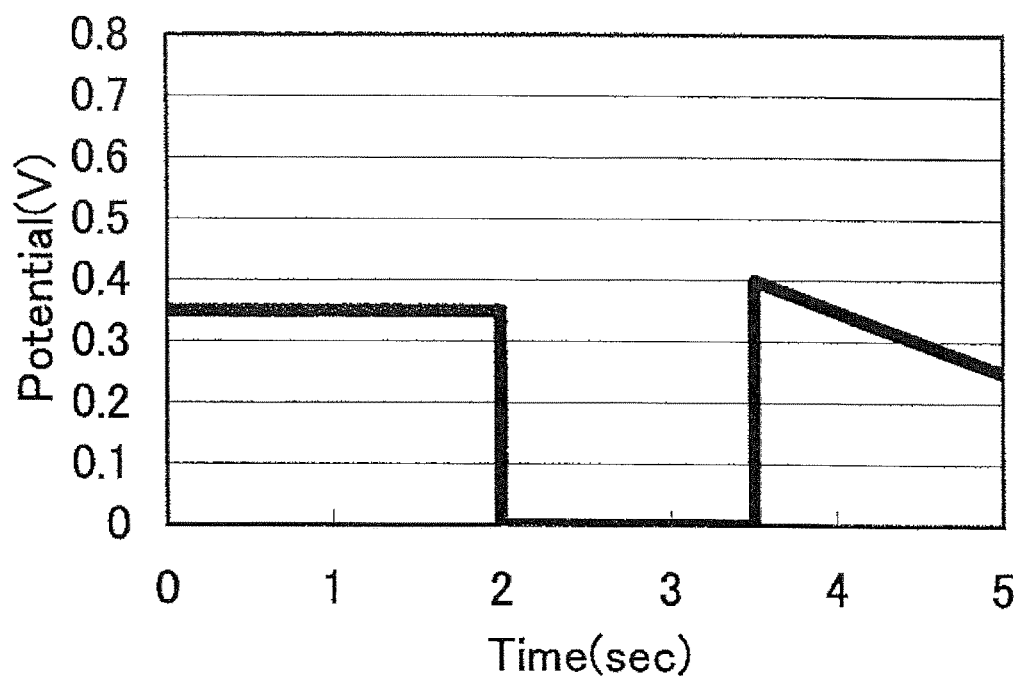
FIG. 23 is a diagram showing a waveform of a voltage that is applied over time in a biological information measurement device according to Thirteenth Embodiment of the present invention.

FIG. 23 shows Embodiment 13 of the present invention. In Embodiment 13, the control unit 21 determines an area from a current value to calculate the biological information value, for example, in the biological information measurement mode C shown in FIG. 3 in the measurement carried out using the biosensor 2 shown in FIG. 2 or the biosensor 2A shown in FIG. 11. That is, FIG. 23 is a diagram showing a waveform of the voltage that is applied over time in a biological information measurement device according to Fourteenth Embodiment of the present invention.

That is, in Embodiment 13, during the biological information measurement mode, with respect to the voltage applying unit, the control unit applies different voltage values between the first input terminal and the second input terminal from the voltage applying unit in the third period and the fourth period of the biological information measurement mode and detects currents flowing between the first input terminal and the second input terminal in the third period and the fourth period, the control unit calculates a current area value from the currents flowing between the first input terminal and the second input terminal in the third period and the fourth period, and the control unit compares the current area value to a standard curve prepared in advance and thereby obtains a biological information measurement value.

Specifically, as shown in FIG. 23, first, the voltage is increased from 0.1 to 0.6 V between 0 and 2.0 seconds, the voltage application is stopped between 2.0 and 3.5 seconds, and then the voltage is increased linearly from 0.1 to 0.25 V between 3.5 and 5 seconds.

In Embodiment 13, the area enclosed by the time-current curve obtained in the biological information measurement mode C is considered as a current area value S. This current area value is highly correlated with the amounts of, for example, glucose, lactic acid, uric acid, bilirubin, and cholesterol contained in a biological sample. Then, the control unit compares the current area value S with the standard curve prepared in advance and thereby calculates the glucose value, lactic acid value, uric acid level, bilirubin level, cholesterol level, etc., i.e., the biological information value.

<Embodiment 14>

Figure 24:
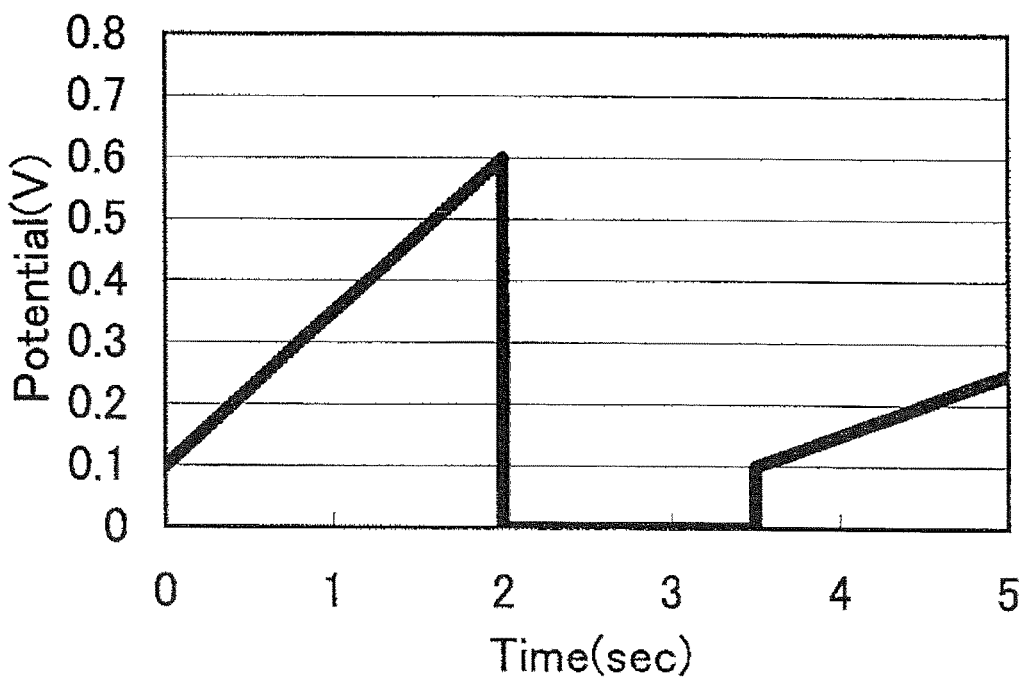
FIG. 24 is a diagram showing a waveform of a voltage that is applied over time in a biological information measurement device according to Fourteenth Embodiment of the present invention.

FIG. 24 shows Embodiment 14 of the present invention. In Embodiment 14, the control unit 21 determines an area from a current value to calculate the biological information value, for example, in the biological information measurement mode C shown in FIG. 3 in the measurement carried out using the biosensor 2 shown in FIG. 2 or the biosensor 2A shown in FIG. 11. That is, FIG. 24 is a diagram showing a waveform of the voltage that is applied over time in a biological information measurement device according to Fourteenth Embodiment of the present invention.

That is, in Embodiment 14, during the biological information measurement mode, with respect to the voltage applying unit, the control unit applies different voltage values between the first input terminal and the second input terminal from the voltage applying unit in the third period and the fourth period of the biological information measurement mode and detects currents flowing between the first input terminal and the second input terminal in the third period and the fourth period, the control unit calculates a current area value from the currents flowing between the first input terminal and the second input terminal in the third period and the fourth period, and the control unit compares the current area value to a standard curve prepared in advance and thereby obtains a biological information measurement value.

Specifically, as shown in FIG. 24, first, the voltage is increased from 0.1 to 0.6 V between 0 and 2.0 seconds, the voltage application is stopped between 2.0 and 3.5 seconds, and then the voltage is increased linearly from 0.1 to 0.25 V between 3.5 and 5 seconds.

In Embodiment 14, the area enclosed by the time-current curve obtained in the biological information measurement mode C is considered as a current area value S. This current area value is highly correlated with the amounts of, for example, glucose, lactic acid, uric acid, bilirubin, and cholesterol contained in a biological sample. Then, the control unit compares the current area value S with the standard curve prepared in advance and thereby calculates the glucose value, lactic acid value, uric acid level, bilirubin level, cholesterol level, etc., i.e., the biological information value.

Embodiment 15

Figure 25:
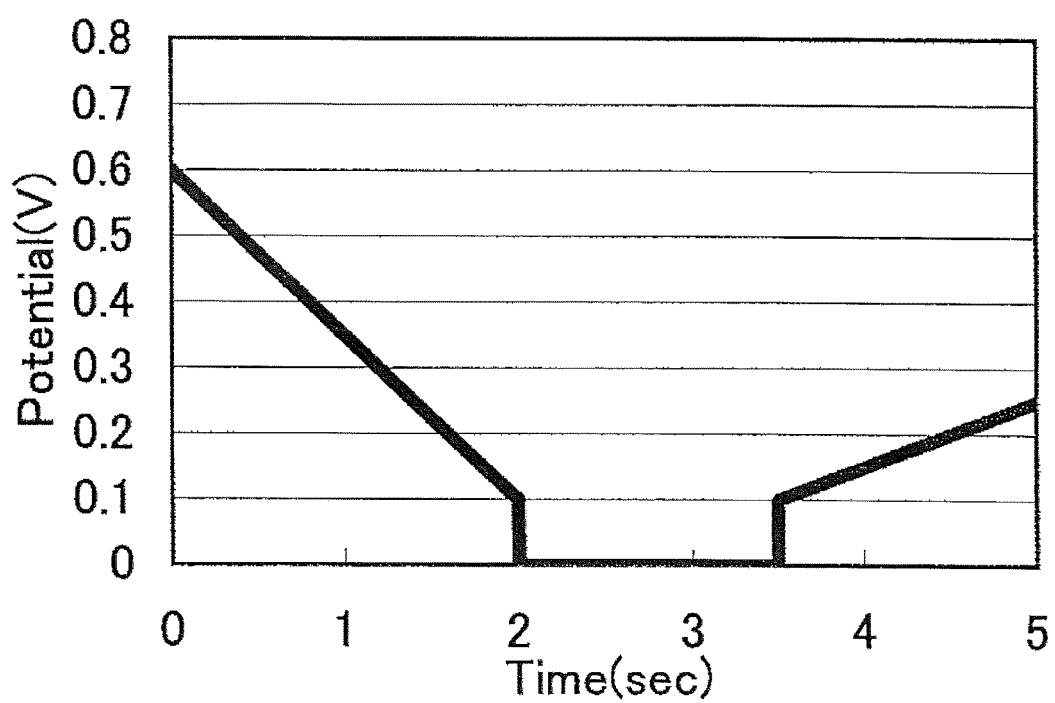
FIG. 25 is a diagram showing a waveform of a voltage that is applied over time in a biological information measurement device according to Fifteenth Embodiment of the present invention.

FIG. 25 shows Embodiment 15 of the present invention. In Embodiment 15, the control unit 21 determines an area from a current value to calculate the biological information value, for example, in the biological information measurement mode C shown in FIG. 3 in the measurement carried out using the biosensor 2 shown in FIG. 2 or the biosensor 2A shown in FIG. 11. That is, FIG. 25 is a diagram showing a waveform of the voltage that is applied over time in a biological information measurement device according to Fourteenth Embodiment of the present invention.

That is, in Embodiment 15, during the biological information measurement mode, with respect to the voltage applying unit, the control unit applies different voltage values between the first input terminal and the second input terminal from the voltage applying unit in the third period and the fourth period of the biological information measurement mode and detects currents flowing between the first input terminal and the second input terminal in the third period and the fourth period, the control unit calculates a current area value from the currents flowing between the first input terminal and the second input terminal in the third period and the fourth period, and the control unit compares the current area value to a standard curve prepared in advance and thereby obtains a biological information measurement value.

Specifically, as shown in FIG. 25, first, the voltage is decreased from 0.6 to 0.1 V between 0 and 2.0 seconds, the voltage application is stopped between 2.0 and 3.5 seconds, and then the voltage is increased linearly from 0.1 to 0.25 V between 3.5 and 5 seconds.

In Embodiment 15, the area enclosed by the time-current curve obtained in the biological information measurement mode C is considered as a current area value S. This current area value is highly correlated with the amounts of, for example, glucose, lactic acid, uric acid, bilirubin, and cholesterol contained in a biological sample. Then, the control unit compares the current area value S with the standard curve prepared in advance and thereby calculates the glucose value, lactic acid value, uric acid level, bilirubin level, cholesterol level, etc., i.e., the biological information value.

As described above, in Embodiment 1 to Embodiment 15, the diagrams showing respective current waveforms were described but the values shown therein are examples and are not necessarily limited to them.

Furthermore, Embodiment 1 to Embodiment 11 each are configured so that in the voltage sweep mode A (the biological information characteristic detection mode), different voltage values are applied between the first input terminal and the second input terminal from the voltage applying unit 15 in the first period and the second period and thereby a plurality of various factors that affect variation in the measurement of biological information are considered as changes in the current value in the voltage sweep mode A (the biological information characteristic detection mode), the biological information correction value is calculated from the changes in the current value, and the biological information measurement value measured during the biological information measurement mode C is corrected by the biological information correction value. Thus, the measurement accuracy can be improved.

In this regard, to describe further, the substances that are affected by the individual differences, storage conditions of the biosensor, variation in the temperature of the biosensor reaction part, technique of applying a drop of blood, etc. each react differently to different voltages. Therefore, as in the present invention, when different voltage values are applied between the first input terminal and the second input terminal from the voltage applying unit 15, the effects on the respective substances are detected beforehand and using the results thereof, the biological information measurement value measured during the biological information measurement mode C is corrected. Thus, the measurement accuracy can be improved.

Embodiments 12 to 15 each are configured as follows: the area enclosed by the time-current curve obtained in the biological information measurement mode C is determined as a current area value and the current area value is compared with the standard curve prepared in advance and thereby a biological information value is obtained. Thus, the system of measuring the biological information to be obtained can be improved.

INDUSTRIAL APPLICABILITY

As described above, the present invention is configured so that in the biological information characteristic detection mode, different voltage values are applied between the first input terminal and the second input terminal from the voltage applying unit in the first period and the second period and thereby a plurality of various factors that affect variation in the measurement of biological information are considered as changes in the current value in the biological information characteristic detection mode, the biological information correction value is calculated from the changes in the current value, and the biological information measurement value measured during the biological information measurement mode is corrected by the biological information correction value. Thus, the measurement accuracy can be improved.

In this regard, to describe further, the substances that are affected by the individual differences, storage conditions of the biosensor, variation in the temperature of the biosensor reaction part, technique of applying a drop of blood, etc. react to different voltages, respectively. Therefore, as in the present invention, when different voltage values are applied between the first input terminal and the second input terminal from the voltage applying unit, the effects on the respective substances are detected beforehand and using the results thereof, the biological information measurement value measured during the biological information measurement mode is corrected. Thus, the measurement accuracy can be improved.

Thus, the present invention is expected to be utilized as, for example, a biological information detection device that detects biological information such as a blood glucose level.

DESCRIPTION OF THE NUMERALS

1 Body Case
2 Biosensor
3 Insertion Opening
4 Insulating Substrate
5 Blood Component Measurement Working Electrode
6 Blood Component Measurement Counter Electrode
7 Input Terminal Portion
8 Reagent Portion
9 Reagent
10 Spacer
11 Cover
12 Blood Supply Path
13 Blood Supply Port
14 Air Hole
15 Voltage Applying Unit
16 Current-Voltage Conversion Part
17 Switching Circuit
18 Application Voltage Part
19 Reference Voltage Part
20 Power Supply Unit
21 Control Unit
22 A/D Conversion Part
23 Determination Means
24 Display Unit
25 Memory Unit
26 Clock
27 Correction Means
28 Blood Component Introduction Detection Electrode

The invention claimed is:

1. A biological information measurement method using a biological information measurement device, to which a biosensor is attached, the biosensor having a first electrode, a second electrode, and a reagent portion provided between the first electrode and the second electrode,
wherein the biological information measurement device comprises:
a first input terminal, to which the first electrode is connected;
a second input terminal, to which the second electrode is connected;
a voltage applying unit for applying a voltage to the first input terminal and the second input terminal; and
a control unit connected to the voltage applying unit, the first input terminal, and the second input terminal,
the control unit is configured to execute a biological information characteristic detection mode and a biological information measurement mode following the biological information characteristic detection mode,
during the biological information characteristic detection mode, with respect to the voltage applying unit, the control unit is configured to apply voltage values between the first input terminal and the second input terminal from the voltage applying unit in a first period and a second period of the biological information characteristic detection mode with the voltage being swept and is configured to detect currents flowing between the first input terminal and the second input terminal in the first period and the second period by the control unit,
the control unit is configured to calculate a biological information correction value from the currents flowing between the first input terminal and the second input terminal in the first period and the second period by the control unit, and
the control unit is configured to correct a biological information measurement value by the biological information correction value, the biological information measurement value being measured during the biological information measurement mode by the control unit,
the method comprising steps of:
with the biosensor being attached, in the biological information characteristic detection mode, applying the voltage to the first input terminal and the second input terminal with the voltage applying unit;
calculating the biological information correction value from a current flowing between the first input terminal and the second input terminal; and
correcting a biological information measurement value measured during the biological information measurement mode by the biological information correction value.

* * * * *